US012676214B2

(12) United States Patent
Bogue et al.

(10) Patent No.: US 12,676,214 B2
(45) Date of Patent: **\*Jul. 7, 2026**

(54) MANAGING PATIENTS OF KNEE SURGERIES

(71) Applicant: 360 Knee Systems Pty Ltd., New South Wales (AU)

(72) Inventors: Emily Bogue, New South Wales (AU); Joshua Twiggs, New South Wales (AU); Willy Theodore, New South Wales (AU); Brad Miles, New South Wales (AU); Bede O'Connor, New South Wales (AU)

(73) Assignee: Kico Knee Innovation Company Pty. Ltd., Frenchs Forest (AU)

( \* ) Notice: Subject to any disclaimer, the term of this patent is extended or adjusted under 35 U.S.C. 154(b) by 0 days.

This patent is subject to a terminal disclaimer.

(21) Appl. No.: 18/585,569

(22) Filed: Mar. 28, 2024

(65) Prior Publication Data

US 2024/0225848 A1 Jul. 11, 2024

Related U.S. Application Data

(63) Continuation of application No. 17/171,197, filed on Feb. 9, 2021, now Pat. No. 11,942,193, which is a
(Continued)

(30) Foreign Application Priority Data

Nov. 5, 2015 (AU) ................................ 2015904543

(51) Int. Cl.
*G16H 10/20* (2018.01)
*A61B 17/92* (2006.01)
(Continued)

(52) U.S. Cl.
CPC ............. *G16H 10/20* (2018.01); *A61B 17/92* (2013.01); *A61F 2/3868* (2013.01);
(Continued)

(58) Field of Classification Search
CPC ........ G16H 10/20; G16H 15/00; G16H 40/63; G16H 50/20; A61B 17/92; A61F 2/3868;
(Continued)

(56) References Cited

U.S. PATENT DOCUMENTS

| | | |
|---|---|---|
| 7,769,763 B1 | 8/2010 | Bem |
| 10,102,926 B1 | 10/2018 | Leonardi |

(Continued)

FOREIGN PATENT DOCUMENTS

| | | | | |
|---|---|---|---|---|
| JP | 2015529359 | 10/2015 | | |
| WO | WO 2013106918 | 7/2013 | | |
| WO | WO-2015054290 A1 * | 4/2015 | ........... | G06F 19/322 |

OTHER PUBLICATIONS

Mannion et al., The role of patient expectations in predicting outcome after total knee arthroplasty, Sep. 12, 2009, Arthritis Research & Therapy, pp. 1-13. (Year: 2009).*
(Continued)

*Primary Examiner* — Christopher L Gilligan
(74) *Attorney, Agent, or Firm* — Nixon Peabody LLP

(57) ABSTRACT

This disclosure relates to systems and methods for managing patients of knee surgeries. A pre-operative patient questionnaire user interface is associated with a future knee operation of the patient. Patient input data is indicative of answers of a patient in relation to the pre-operative patient questionnaire. A processor of a computer system evaluates a statistical model to determine a predicted satisfaction value indicative of satisfaction of the patient with the future knee operation. The statistical model comprises nodes stored on data memory representing the patient input data and the
(Continued)

predicted satisfaction value, and edges stored on data memory between the nodes representing conditional dependencies between the patient input data and the predicted satisfaction value. The processor then generates an electronic document comprising a surgeon report associated with the future knee operation to indicate to the surgeon the predicted satisfaction value.

20 Claims, 13 Drawing Sheets

Related U.S. Application Data continuation of application No. 15/772,872, filed as application No. PCT/AU2016/051043 on Nov. 3, 2016, now Pat. No. 10,984,893.

(51) Int. Cl.

| | |
|---|---|
| *A61F 2/38* | (2006.01) |
| *A61F 2/46* | (2006.01) |
| *G06N 3/02* | (2006.01) |
| *G06N 3/042* | (2023.01) |
| *G06N 7/00* | (2023.01) |
| *G16H 15/00* | (2018.01) |
| *G16H 40/63* | (2018.01) |
| *G16H 50/20* | (2018.01) |

(52) U.S. Cl.
CPC ............. *A61F 2/4684* (2013.01); *G06N 3/02* (2013.01); *G06N 3/042* (2023.01); *G06N 7/00* (2013.01); *G16H 15/00* (2018.01); *G16H 40/63* (2018.01); *G16H 50/20* (2018.01); *A61F 2002/3895* (2013.01); *A61F 2002/4687* (2013.01)

(58) Field of Classification Search
CPC ............ A61F 2/4684; A61F 2002/3895; A61F 2002/4687; G06N 3/02; G06N 3/042; G06N 7/00
See application file for complete search history.

(56) References Cited

U.S. PATENT DOCUMENTS

| | | | |
|---|---|---|---|
| 10,984,893 B2 | 4/2021 | Bogue | |
| 2004/0133463 A1 | 7/2004 | Benderev | |
| 2008/0172214 A1 | 7/2008 | Col | |
| 2010/0332194 A1 | 12/2010 | McGuan | |
| 2013/0035951 A1 | 2/2013 | Frey | |
| 2013/0185310 A1 | 7/2013 | De Guise | |
| 2013/0332128 A1* | 12/2013 | Miles | G16H 50/50 |
| | | | 703/6 |

| | | | |
|---|---|---|---|
| 2014/0013565 A1* | 1/2014 | MacDonald | G16H 50/70 |
| | | | 703/11 |
| 2014/0046682 A1 | 2/2014 | Soto | |
| 2014/0052465 A1 | 2/2014 | Madan | |
| 2014/0108322 A1* | 4/2014 | Buchanan | G06N 5/02 |
| | | | 706/50 |
| 2014/0244220 A1 | 8/2014 | McKinnon | |
| 2014/0244292 A1 | 8/2014 | Rosenberg | |
| 2015/0072327 A1 | 3/2015 | Beaulieu | |
| 2015/0088541 A1* | 3/2015 | Yao | G06Q 10/10 |
| | | | 705/2 |
| 2015/0286784 A1* | 10/2015 | Hagigi | G16H 50/20 |
| | | | 705/2 |
| 2015/0324530 A1 | 11/2015 | Heywood | |
| 2016/0283676 A1* | 9/2016 | Lyon | G06Q 40/08 |
| 2018/0330800 A1 | 11/2018 | Bogue | |

OTHER PUBLICATIONS

Eskinazi et al., An Open-Source Toolbox for Surrogate Modeling of Joint Contact Mechanics, Feb. 2016, IEEE Transactions on Biomedical Engineering, vol. 63, No. 2, pp. 269-277. (Year: 2016).*

Huang et al., Kinematics and Mechanical Properties of Knees following Patellar Replacing and Patellar Retaining Total Knee Arthroplasty, Nov. 10, 2015, Hindawi Publishing Corporation Applied Bionics and Biomechanics, vol. 2015, Article ID 391450, pp. 1-10. (Year: 2015).*

International Search Report and Written Opinion issued in PCT/AU2016/051043, Jan. 10, 2017, 11 pages.

Jahandar, "Concurrent Simulation of a Subject Specific Musculoskeletal Model with Anatomical Knee," Pro Quest, No. 10178614, Jul. 2015, pp. 1-105.

Mannion et al. "The Role of Patient Expectations in Predicting Outcome After Total Kenee Arthroplasty," Arthritis Research & Therapy, Sep. 21, 2009, pp. 1-13.

Miller et al. "total Knee Arthroplasty Component Templating," The Journal of Arthroplasty, vol. 27, No. 9, pp. 1707-1709, 2012.

U.S. Appl. No. 15/772,872, Final Office Action, Mailed Nov. 2, 2020, 20 pages.

U.S. Appl. No. 15/772,872, Non-Final Office Action, Mailed Mar. 30, 2020, 20 pages.

U.S. Appl. No. 15/772,872, Notice of Allowance, Mailed Feb. 11, 2021, 9 pages.

Japanese Application No. JP 2018-543410, Office Action, Mailed Apr. 17, 2020, 19 pages with translation.

"Business Intelligence", Ma Gang, pp. 293-304, Dongbei University of Finance & Economics Press, Jul. 2010.

"Orthopaedic Knowledge Update Hip and Knee Reconstruction", Robert L et al., pp. 13-24, People's Military Medical Press, Sep. 2009.

"Patient's preoperative expectation and surgeon's satisfaction versus Patient's postoperative satisfaction after total knee arthroplasty", Yu Benfeng, Chinese Master's Theses Full-text Database—Series of Medical and Health Sciences, 2012, Issue 10, pp. E066-368, published Oct. 15, 2012.

* cited by examiner

100

120

120

122    114

104

108 prog data

112

110

102        106

73% satisfaction
probability  130

116

150

151    100  154  112

64%

152

153

200

201 — generating a pre-operative patient questionnaire user interface

202 — receiving patient input data

203 — evaluating by a processor of a computer system a statistical model

204 — generating an electronic document

1300

MANAGING PATIENTS OF KNEE SURGERIES

CROSS-REFERENCE TO RELATED APPLICATIONS

This application is a continuation of U.S. patent application Ser. No. 17/117,197 filed on Feb. 9, 2021, now allowed, which is a continuation of U.S. patent application Ser. No. 15/772,872, filed on May 2, 2018, now issued U.S. Pat. No. 10,984,893 on Apr. 20, 2021, which claims priority from Australian National Stage of International Application No. PCT/AU2016/051043 filed on Nov. 3, 2016, which claims priority from AU 201590543 filed on Nov. 5, 2015. Each of these applications is hereby incorporated herein by reference in its entirety for all purposes, the disclosure of each of which is hereby incorporated by reference herein in its entirety.

TECHNICAL FIELD

This disclosure relates to systems and methods for managing patients of knee surgeries.

BACKGROUND

Osteoarthritis is the degenerative loss of cartilage tissue in a joint, and is the most common joint disease in the Australian community with approximately 15% of the population adversely affected. Of these, the knee is a common site for osteoarthritic symptoms to emerge, which can cause debilitating pain and loss of functional ability for the sufferer. Incidence increases dramatically with age, with as many as ⅓ of people showing radiographic evidence of knee osteoarthritis in the 60-69 years age group, though a smaller portion suffer symptomatically. As such, the growth in this demographic group in line with the aging population and the consequent increase in work demands placed upon this population group are contributing to an acceleration in the incidence of knee osteoarthritis across the population as a whole. Incidence is also increasing among younger age groups associated with risk factors such as obesity, joint injury and repetitive stress on the joint as a result of physical labour, further contributing to the burgeoning societal burden of knee osteoarthritis.

One treatment for end-stage knee osteoarthritis is Total Knee Arthroplasty (TKA). One goal is to effect pain relief and recover functional ability for the sufferer. As a result of the enormous benefit that can be delivered to patients in terms of lifestyle improvement and work capability, the surgery is considered to be highly successful. The primary objective measure for success is survivor analysis with regards to revision rate, which sits at 6.5% over a 12 year window. Interestingly, this figure is vulnerable to underestimation as the conventional tracking of a patient endpoint when they undergo revision surgery implies two other success conditions: either the patient dies before undergoing a revision surgery they may require in the future or a patient's health deteriorates with age to the point where it is deemed safer not to operate even if a revision surgery is required. Nevertheless, this statistic masks a greater problem: as many as 20% of patients report dissatisfaction with the pain relief and functional outcomes of their surgery after 1 year. Due to the relative ease of data collection and hence wider adoption in joint registries of survivorship based data, as well as the relatively greater exposure of the practicing surgeon to a smaller number of highly dissatisfied patients affected by outcomes such as implant loosening than a larger number of less dissatisfied patients, there exists the potential for a bias in favour of mechanically 'safer' but not necessarily patient outcome optimal surgical decision making.

When considering survivorship with a wider range of endpoints incorporating negative pain or functional outcomes over time, the effective survivorship rate has been shown to be about half of all patients.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

A method for managing patients of knee surgeries comprises:

generating a pre-operative patient questionnaire user interface associated with a future knee operation of the patient;

receiving patient input data indicative of answers of a patient in relation to the pre-operative patient questionnaire;

evaluating by a processor of a computer system a statistical model to determine a predicted satisfaction value indicative of satisfaction of the patient with the future knee operation, the statistical model comprising:

nodes stored on data memory representing the patient input data and the predicted satisfaction value, and edges stored on data memory between the nodes representing conditional dependencies between the patient input data and the predicted satisfaction value; and generating an electronic document comprising a surgeon report associated with the future knee operation to indicate to the surgeon the predicted satisfaction value.

Since the patient input data and the predicted satisfaction value are represented by nodes and the conditional dependencies are represented by edges, disparate data sources indicative of the conditional dependencies can be integrated, which is not possible with other solutions. The advantage is a more accurate prediction model, which means patients can be managed more realistically leading to increased patient satisfaction with their knee surgery.

The satisfaction value may be indicative of a probability of satisfaction.

The statistical model may be a Bayesian Network.

The method may further comprise determining multiple influencing factors, wherein generating the surgeon report comprises generating a quantitative indication of the multiple influencing factors.

Determining the multiple influencing factors may comprise determining the multiple influencing factors from patient reported outcome measures.

The patient reported outcome measures may include one or more of the Oxford Knee Score and the he Western Ontario and McMaster Universities Arthritis Index (WOMAC).

Determining the multiple influencing factors may comprise determining influencing factors from the Knee injury and Osteoarthritis Outcome Score (KOOS).

Determining influencing factors from the KOOS may comprise determining influencing factors of one or more of: pain, symptoms, function in daily living (ADL), function in sport and recreation, and knee related quality of life (QOL).

Generating the surgeon report may comprise determining a statistical transformation of the predicted satisfaction value.

The statistical transformation may comprise scaling to patient distributions of answers.

The distribution of answers may be drawn from one or more of: postoperative outcome, preoperative baseline, healthy patient baseline, postoperative high achievers, and postoperative low achievers.

The statistical transformation may comprise a conversion to one or more of:

odds ratio and risk factors.

Generating the surgeon report may comprise generating a graphical depiction of one or more of:

boxes, vertical bars, horizontal bars, graphical elements with a colour scale mapped visual output, conversion to percentages, embedding into customizable lines of text, and specific highlighted risk factors indicated to patients.

The nodes of the statistical model may be hierarchical with at least one path from the patient input data to the predicted satisfaction value having at least two edges.

The method may further comprise:

generating an expert user interface comprising an expert data input for expert input data indicative of the conditional dependencies between the patient input data and the predicted satisfaction value;

receiving the expert input data;

determining the conditional dependencies between the patient input data and the predicted satisfaction value based on the expert input data; and storing the conditional dependencies as part of the statistical model on a data store.

Determining the conditional dependencies may be based on expert network modelling and expert opinion as reflected by the expert input data.

The expert input data may comprise data from an expert including one or more of:

a surgeon, a patient, a nurse, a physiotherapist, a psychologist, and an allied health professional.

The method may further comprise automatically determining an intervention procedure based on the predicting satisfaction value, wherein generating the surgeon report comprises generating an indication of the intervention procedure.

The method may further comprise after the knee operation:

generating a post-operative patient questionnaire user interface associated with the knee operation;

receiving post-operative patient input data indicative of answers of the patient in relation to the post-operative patient questionnaire; and determining updated conditional dependencies between the patient input data and the predicted satisfaction value based on the post-operative patient input data.

The method may further comprise:

receiving intra-operative data and post-operative data;

determining after the knee operation a revised predicted satisfaction value based on the intra-operative data and the post-operative data.

The pre-operative patient questionnaire or a postoperative patient questionnaire may comprise multiple pages and each page contains exactly one question.

Each page may comprise one or more of visual Analog Scale, binary or multiple choice, open text or number fields, and customizable on a per surgeon, per practice or per site basis to enter the patient input data.

The method may further comprise:

determining a cost of an error as measured in terms of patient outcomes;

determining future outcome gains or losses; and determining subsequent treatment decisions based on the future outcome gains or losses.

The surgeon report may comprise an indication of one or more of generic/holistic measures of health, specific functional attainments, postoperative range of motion, postoperative time to mobilisation, ambulation, activity level, and risk of adverse events.

The method may further comprise receiving kinematic simulation data from a simulator that simulates the result of reconstruction of the total knee replacement, wherein the patient input data is indicative of activity desires or patient behaviour, and the nodes of statistical model comprise nodes representing the kinematic simulation data and the patient input data indicative of activity desires or patient behaviour.

The method may further comprise:

generating a model selection user interface comprising multiple indications associated with respective models, each of the respective models being associated with different conditional dependencies between the nodes of the statistical model;

receiving user input in relation to one or more of the multiple indications associated with one or more of the models;

determining a price value associated with the one or more of the models;

generating a payment interface for the determined price value; and upon receiving a payment confirmation enabling the evaluation of the one or more of the mode The method may further comprise pre-operative and/or post-operative patient monitoring data, wherein the statistical model comprises further nodes and edges for the pre-operative and/or post-operative monitoring data.

The pre-operative and/or post-operative patient monitoring data may relate to a number of steps taken by the patient over a predetermined period of time.

The method may further comprise receiving data from multiple data sources;

receiving a weight associated with each of the multiple data sources;

determining for each of the multiple data sources a predicted satisfaction value; and determining a weighted satisfaction value based on the predicted satisfaction values and the associated weights.

Receiving the weight may comprise receiving the weight from an expert through a user interface. The multiple data sources may include one or more of simulated outcomes, pre-operative and post-operative monitoring, expert knowledge models and data constructed models.

A method for operating a healthcare system comprises:

performing the method of any one of the preceding claims to determine a predicted satisfaction value for each of multiple patients enrolled in the healthcare system;

determining a patient care item for each of the multiple patients by maximising utility of healthcare spent in the healthcare system.

Maximising utility may comprise one or more of global cost minimisation with a collective satisfaction or patient outcome target per patient cost minimisation with a per patient satisfaction or patient outcome target, and fixed global cost allocation with a satisfaction or patient outcome target maximisation Maximising utility may be based on a predetermined amount for each of the multiple patients.

A computer system for managing patients of knee surgeries comprises:

a screen;

an input device to receive patient input data from the patient;

data memory to store a statistical model comprising:

nodes representing the patient input data and a predicted satisfaction value, and edges between the nodes representing conditional dependencies between the patient input data and the predicted satisfaction value; and a processor to generate on the screen a pre-operative patient questionnaire user interface associated with a future knee operation of the patient;

receive from the input device patient input data indicative of answers of a patient in relation to the pre-operative patient questionnaire;

evaluate the statistical model to determine a predicted satisfaction value indicative of satisfaction of the patient with the future knee operation; and generate an electronic document comprising a surgeon report associated with the future knee operation to indicate to the surgeon the predicted satisfaction value.

Optional features described of any aspect of method, computer readable medium or computer system, where appropriate, similarly apply to the other aspects also described here.

BRIEF DESCRIPTION OF DRAWINGS

An example will be described with reference to.

6

Figure 2:
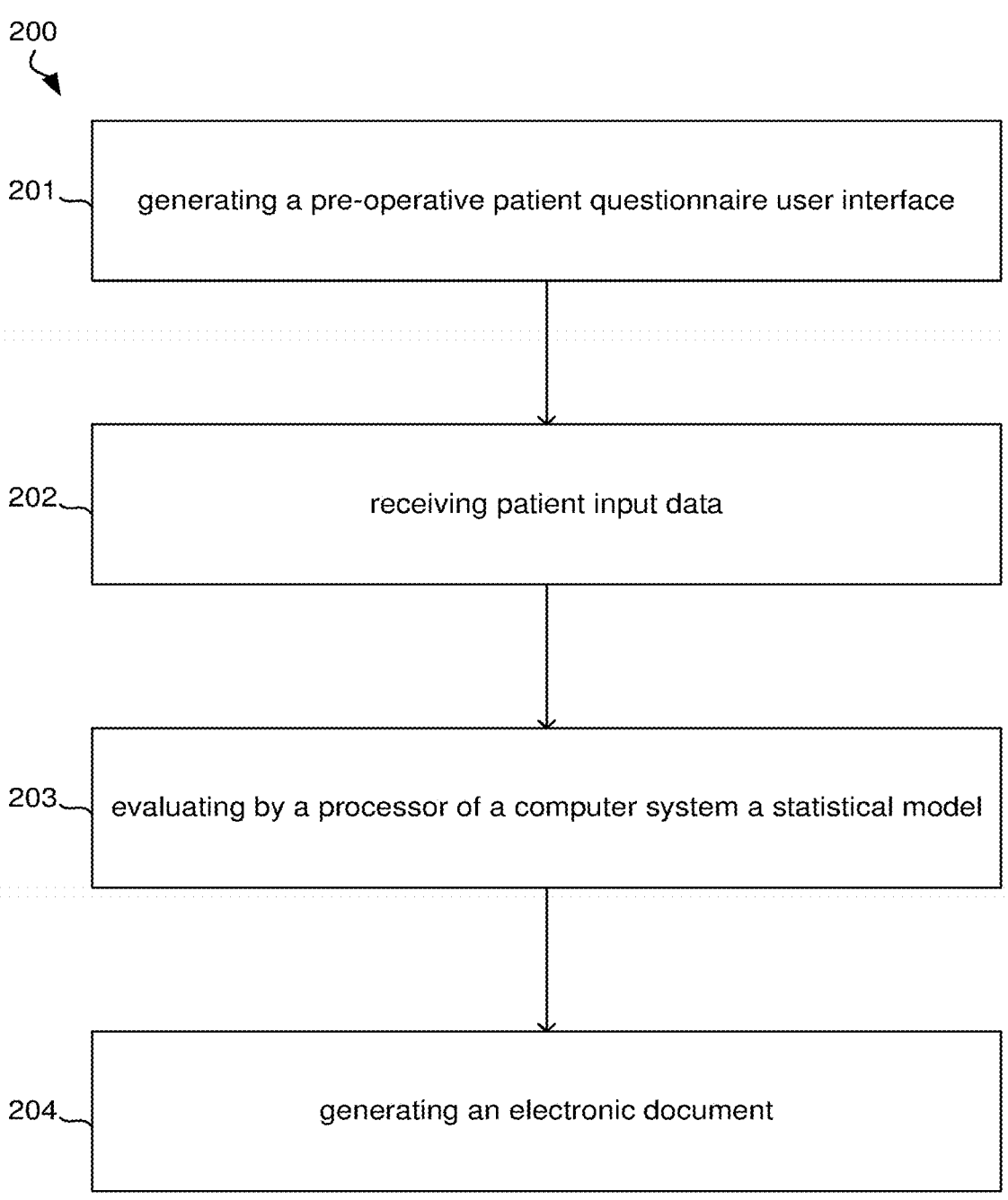

FIG. 2 illustrates a method for managing patients of knee surgeries.

Figure 3:
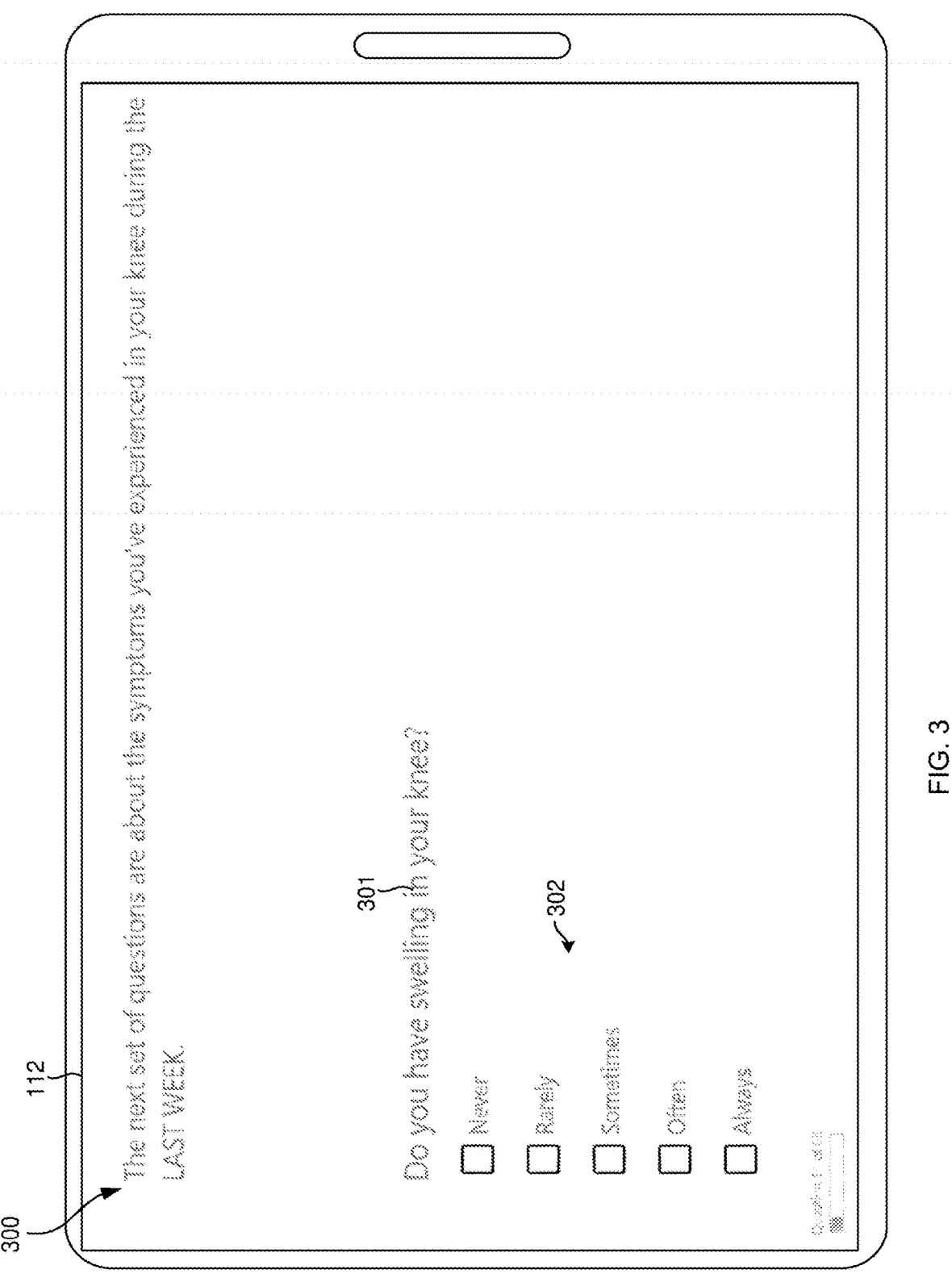

FIG. 3 illustrates an example pre-operative patent questionnaire user interface.

Figure 4:
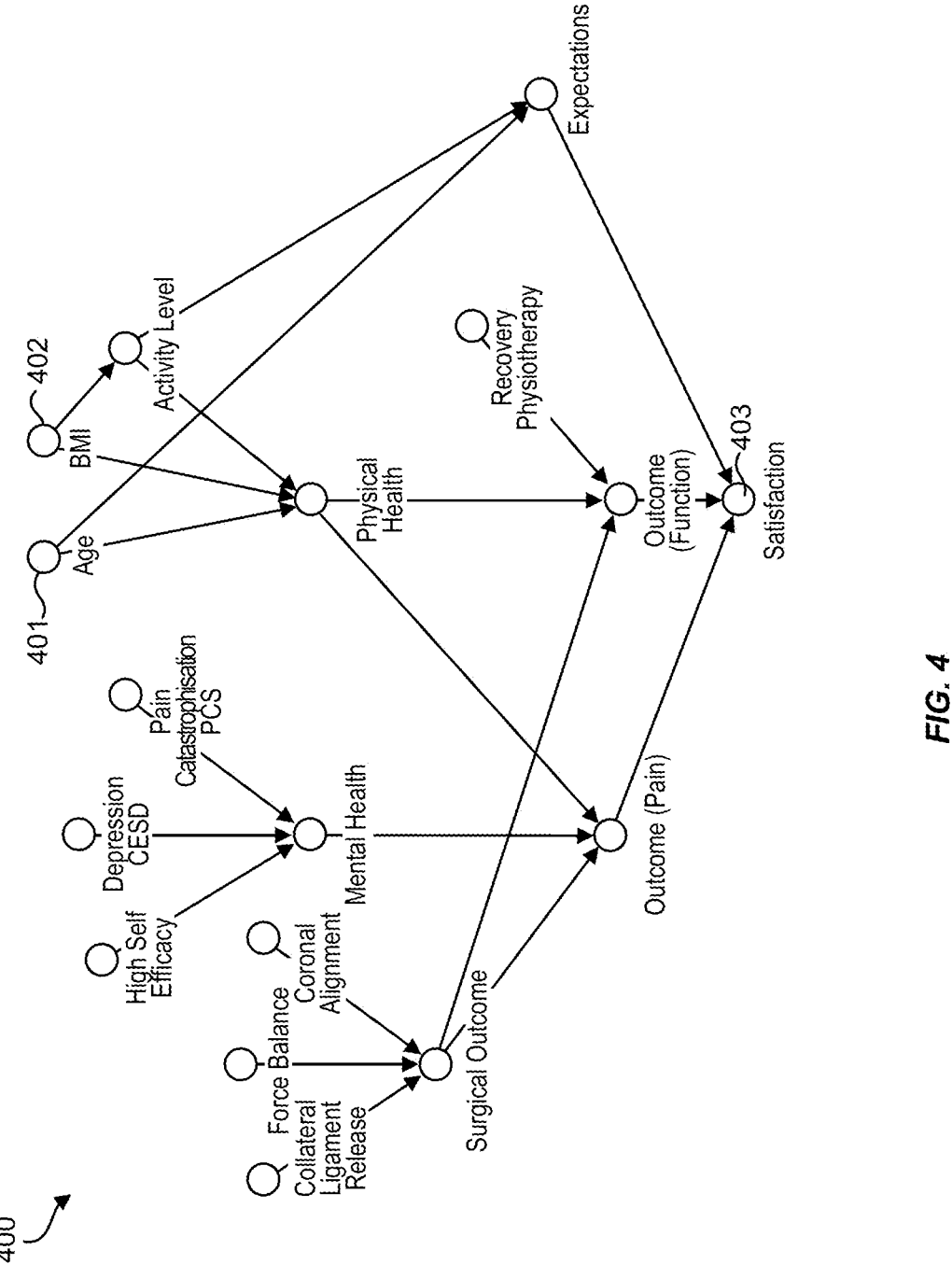

FIG. 4 illustrates a statistical model.

Figure 5:
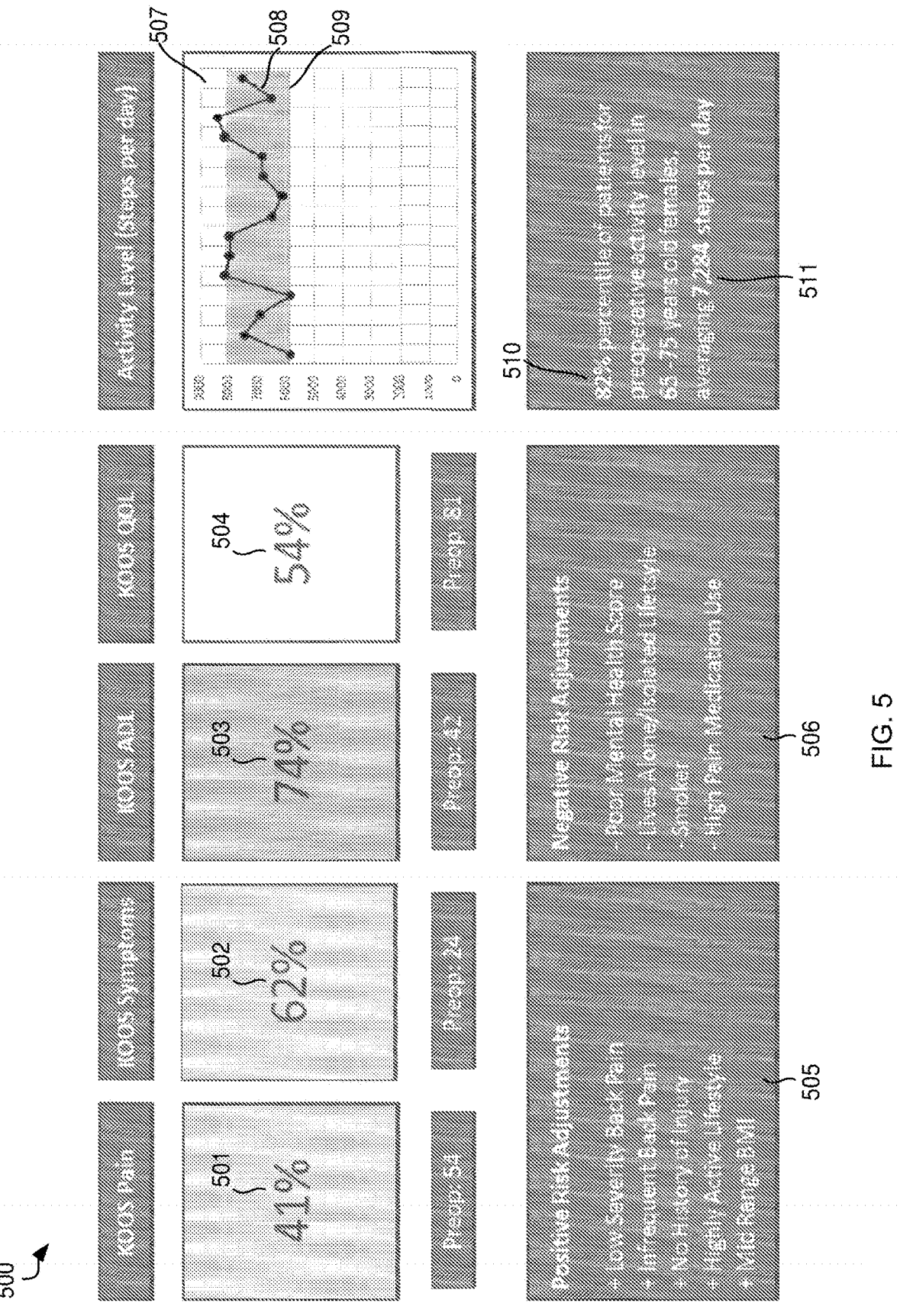

FIG. 5 illustrates an example surgeon report.

Figure 6:
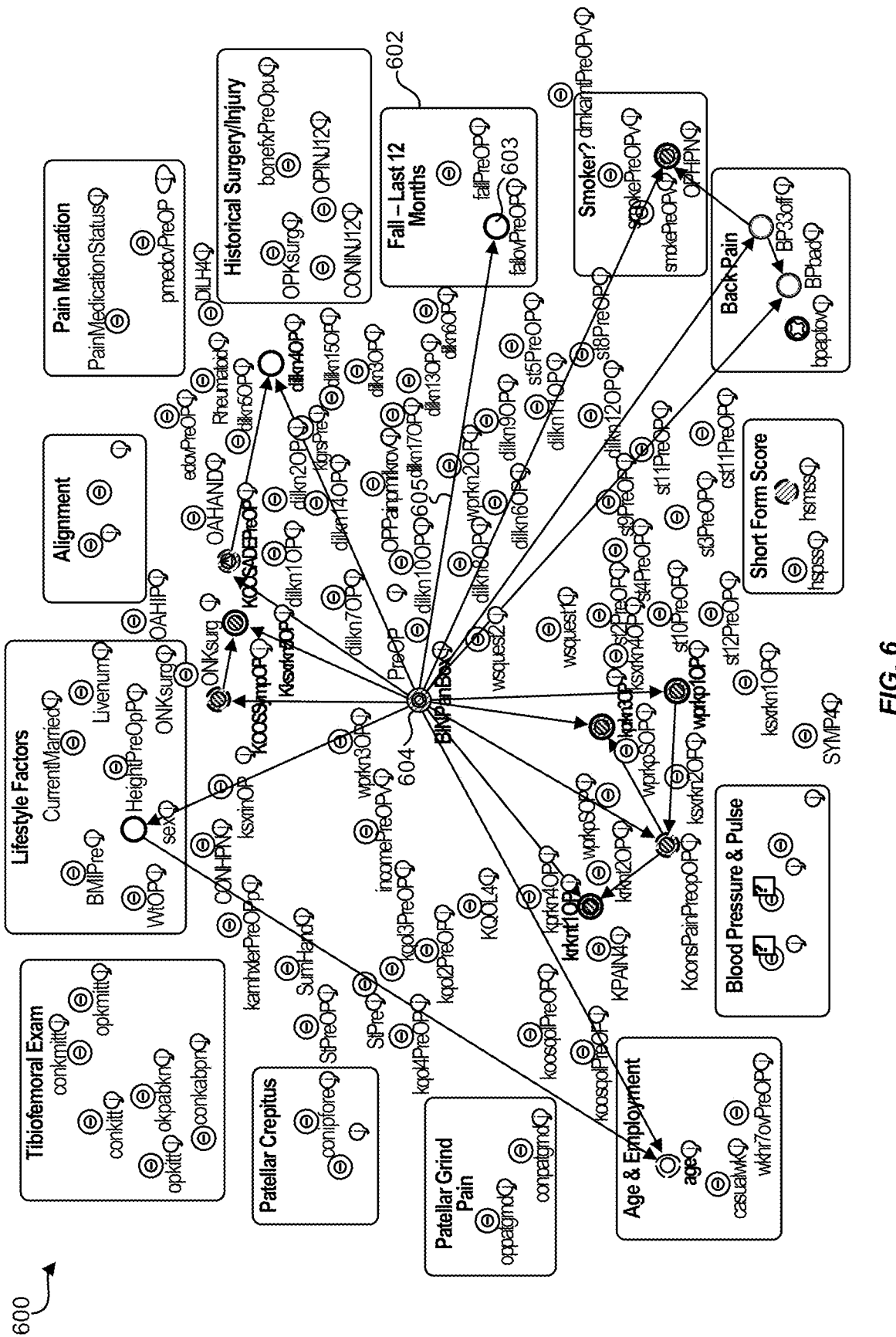

FIG. 6 illustrates another example of the statistical model.

Figure 7:
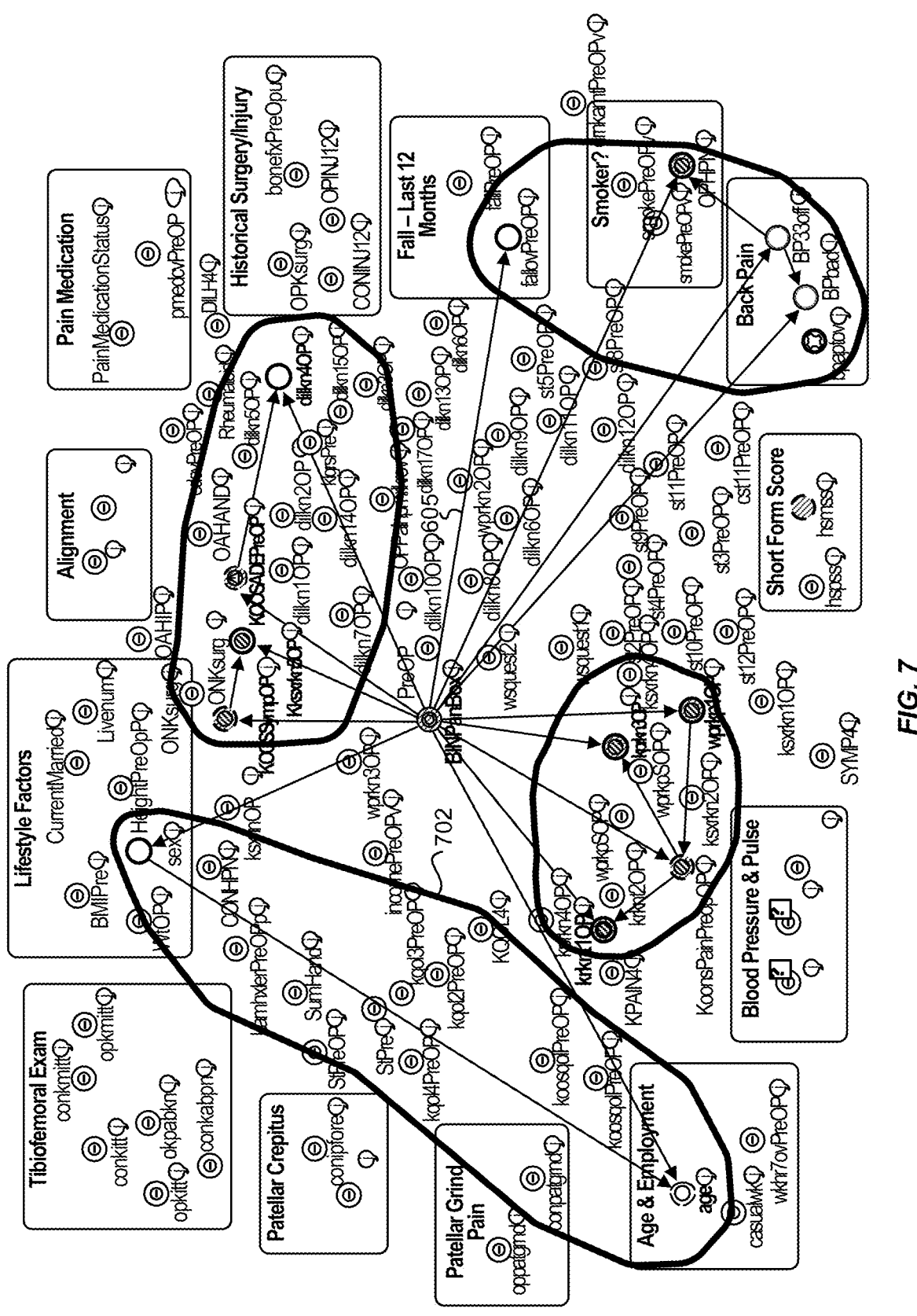

FIG. 7 illustrates the statistical model from FIG. 6 in more detail.

Figure 8:
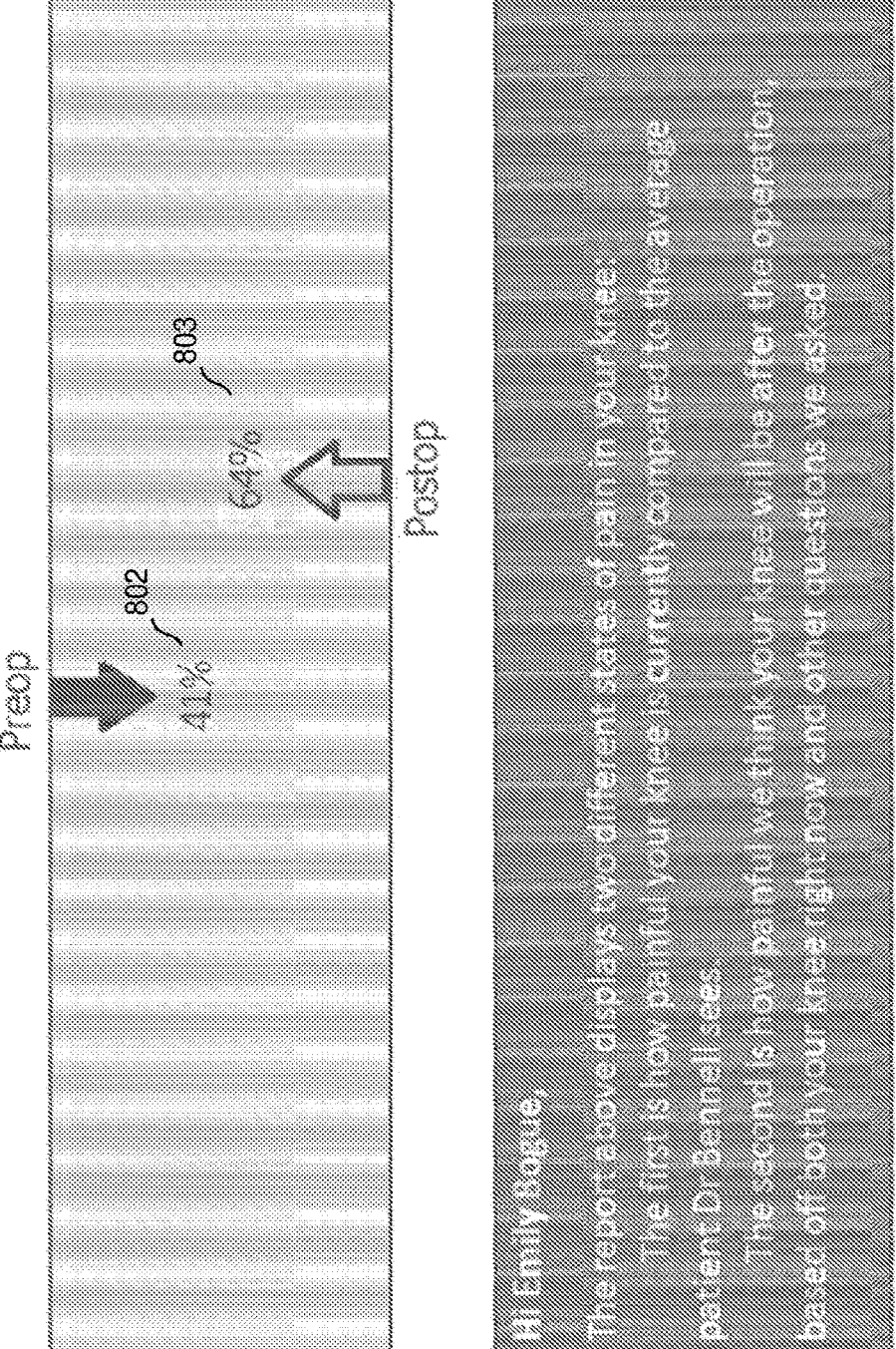

FIG. 8 illustrates another example of a report.

Figure 9:
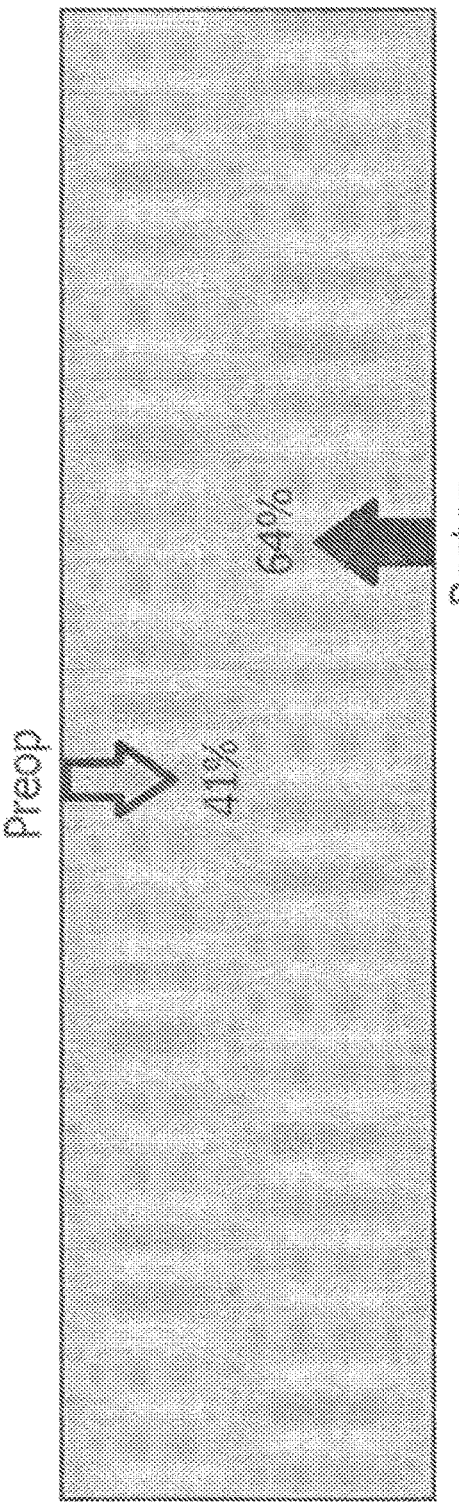
Figure 9:
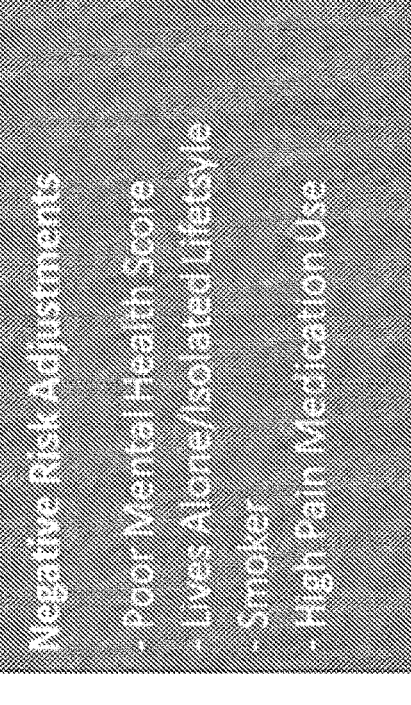
Figure 9:
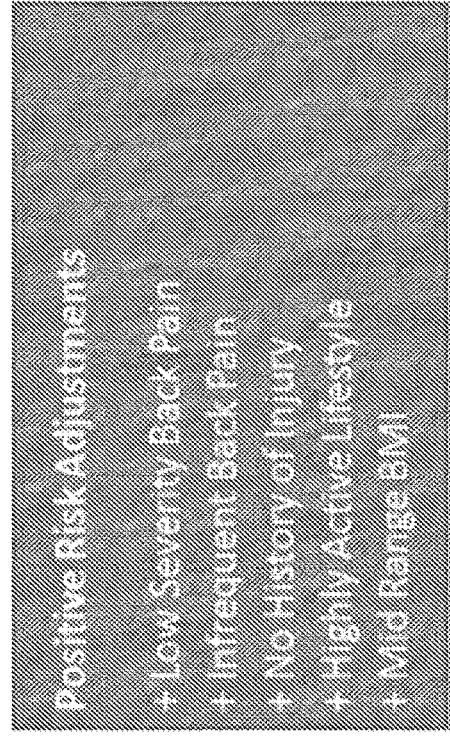

FIG. 9 illustrates another report as a result of user interaction with an interactive element in report of FIG. 8.

Figure 10:
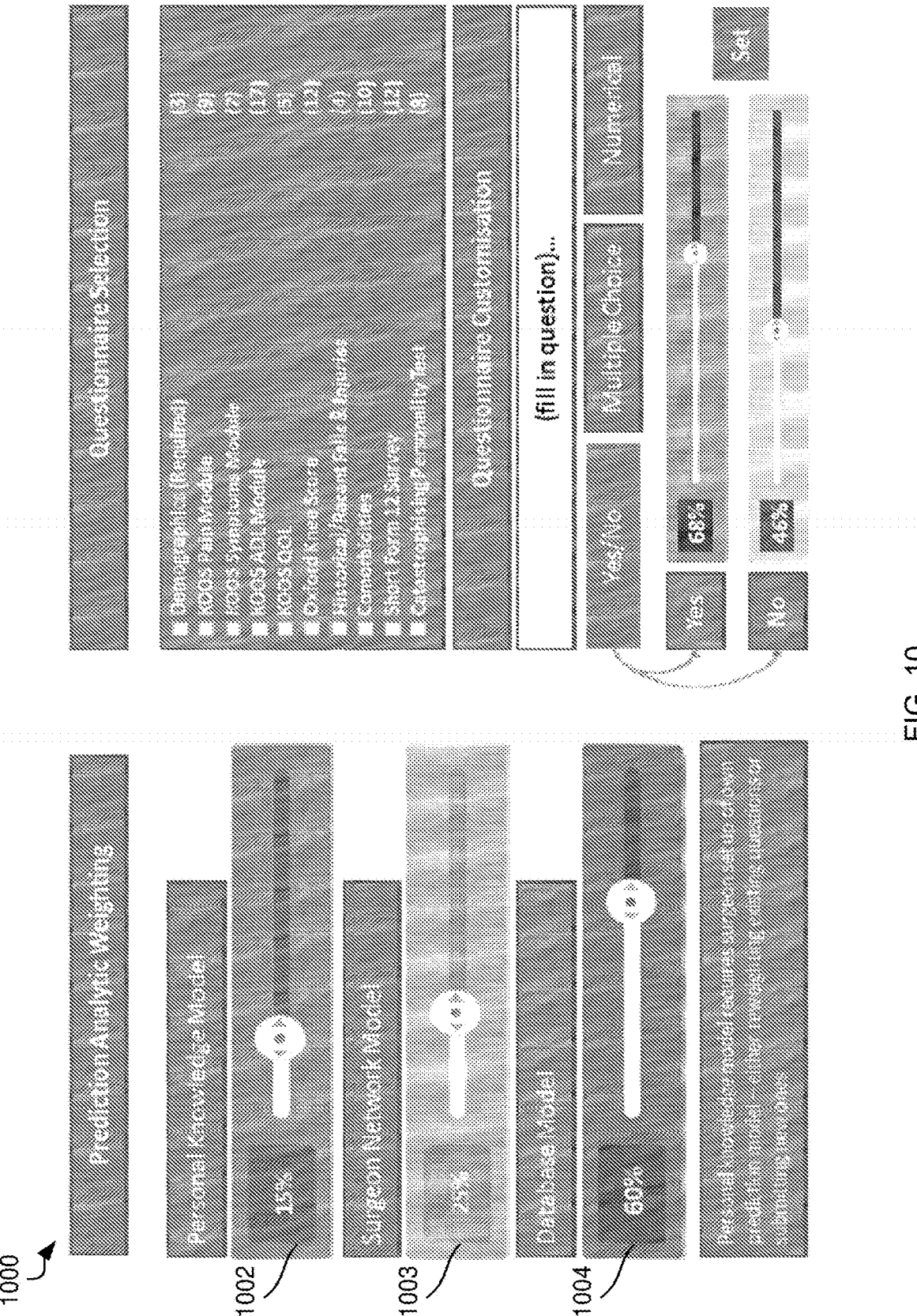

FIG. 10 illustrates an example of a 'settings' back page.

Figure 11:
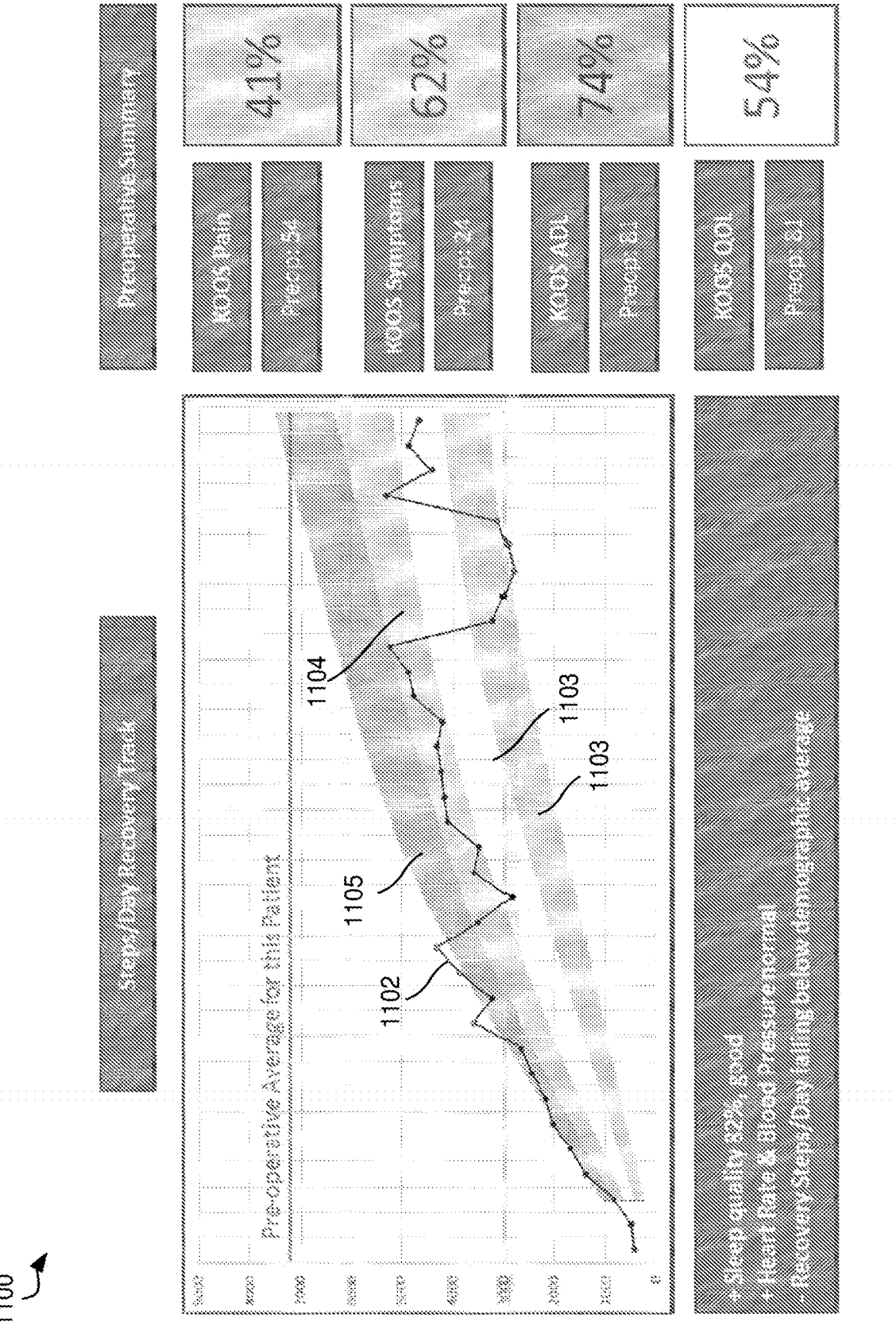

FIG. 11 illustrates a postoperative monitoring user interface.

Figure 12:
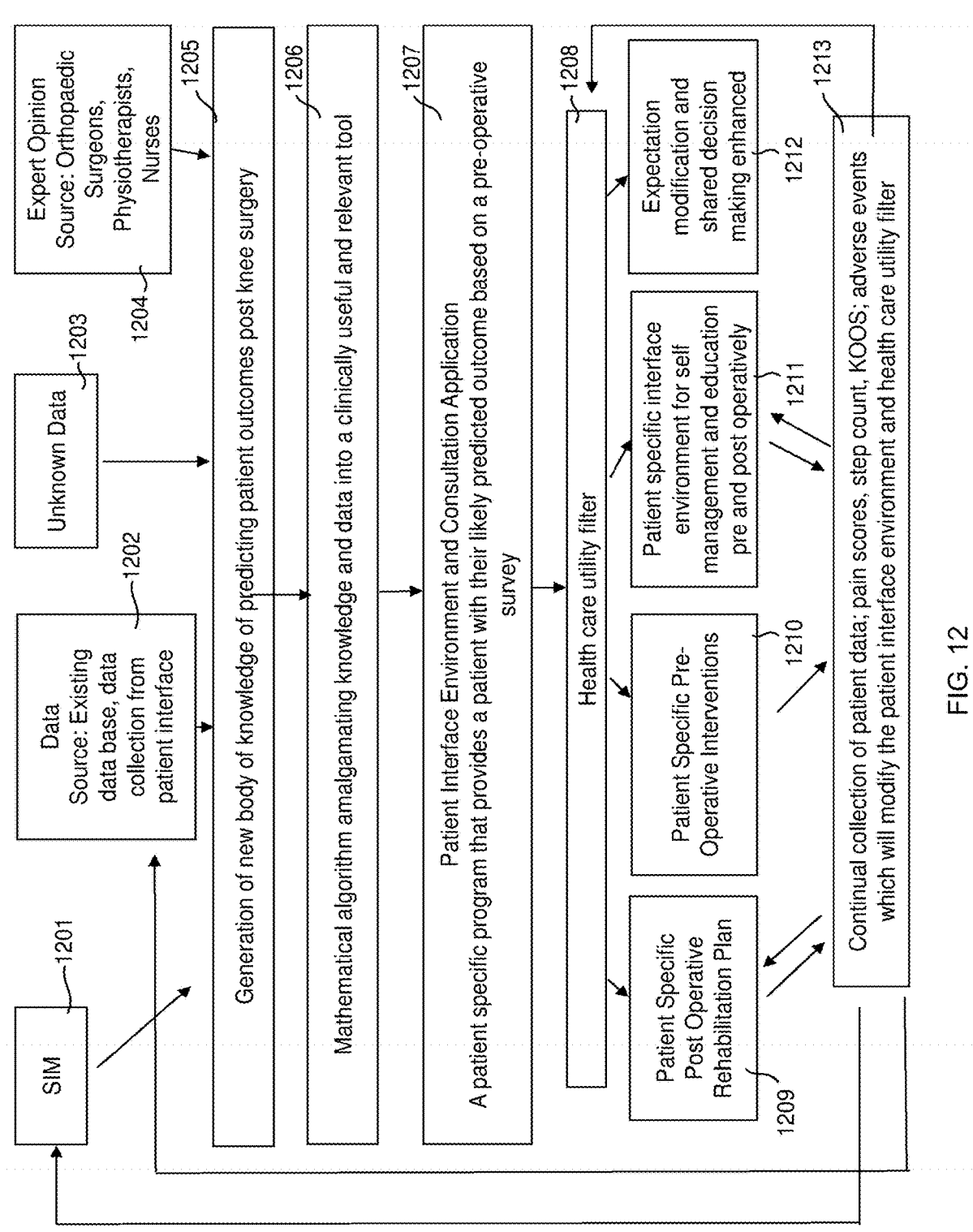

FIG. 12 illustrates an architecture for managing patients of knee surgeries.

Figure 13:
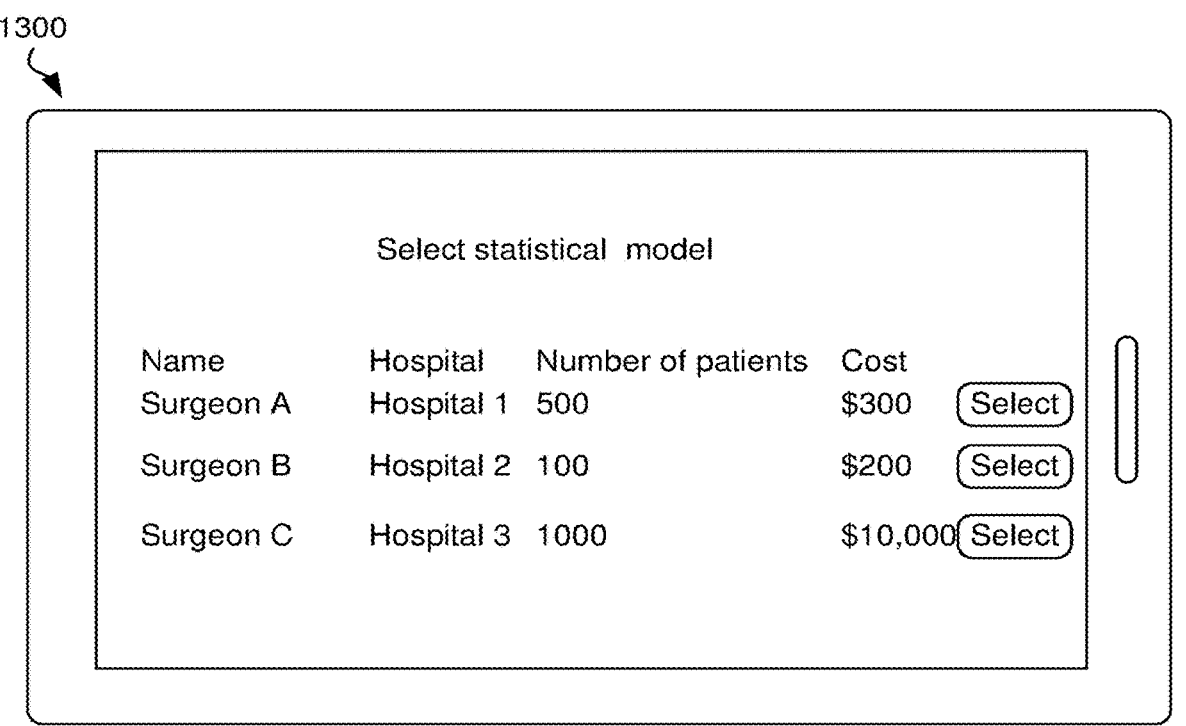

FIG. 13 illustrates a model selection user interface.

DESCRIPTION OF EMBODIMENTS

FIG. 1 illustrates a computer system 100 for managing patients of knee surgeries. The computer system 100 comprises a processor 102 connected to a program memory 104, a data memory 106, a communication port 108 and a user port 110. The program memory 104 is a non-transitory computer readable medium, such as a hard drive, a solid state disk or CD-ROM. Software, that is, an executable program stored on program memory 104 causes the processor 102 to perform the method in FIG. 2, that is, processor 102 receives patent input data, evaluates a statistical model to determine a predicted satisfaction value and generates an electronic document comprising a surgeon report.

The processor 102 may then store the predicted satisfaction value and the report on data store 106, such as on RAM or a processor register. Processor 102 may also send the report via communication port 108 to a server, such as patient management database to be displayed to the surgeon by request.

The processor 102 may receive data, such as the patient input data, from data memory 106 as well as from the communications port 108 and the user port 110, which is connected to a display 112 that shows a visual representation 114 of the electronic document to a surgeon 116 or other user or operator. In one example, processor 102 receives patient input data from a webserver that hosts a questionnaire via communications port 108, such as by using a Wi-Fi network according to IEEE 802.11. The Wi-Fi network may be a decentralised ad-hoc network, such that no dedicated management infrastructure, such as a router, is required or a centralised network with a router or access point managing the network.

Although communications port 108 and user port 110 are shown as distinct entities, it is to be understood that any kind of data port may be used to receive data, such as a network connection, a memory interface, a pin of the chip package of processor 102, or logical ports, such as IP sockets or parameters of functions stored on program memory 104 and executed by processor 102. These parameters may be stored on data memory 106 and may be handled by-value or by-reference, that is, as a pointer, in the source code.

The processor 102 may receive data through all these interfaces, which includes memory access of volatile memory, such as cache or RAM, or non-volatile memory, such as an optical disk drive, hard disk drive, storage server or cloud storage. The computer system 100 may further be implemented within a cloud computing environment, such as a managed group of interconnected servers hosting a dynamic number of virtual machines.

It is to be understood that any receiving step may be preceded by the processor 102 determining or computing the data that is later received. For example, the processor 102 determines input data and stores the input data in data memory 106, such as RAM or a processor register. The processor 102 then requests the data from the data memory 106, such as by providing a read signal together with a memory address. The data memory 106 provides the data as a voltage signal on a physical bit line and the processor 102 receives the input data via a memory interface.

It is to be understood that throughout this disclosure unless stated otherwise, nodes, edges, graphs, solutions, variables, surgery plans, dimensions, locations and the like refer to data structures, which are physically stored on data memory 106 or processed by processor 102. Further, for the sake of brevity when reference is made to particular variable names, such as "predicted satisfaction value", this is to be understood to refer to values of variables stored as physical data in computer system 100.

Figures 1A, 1B:
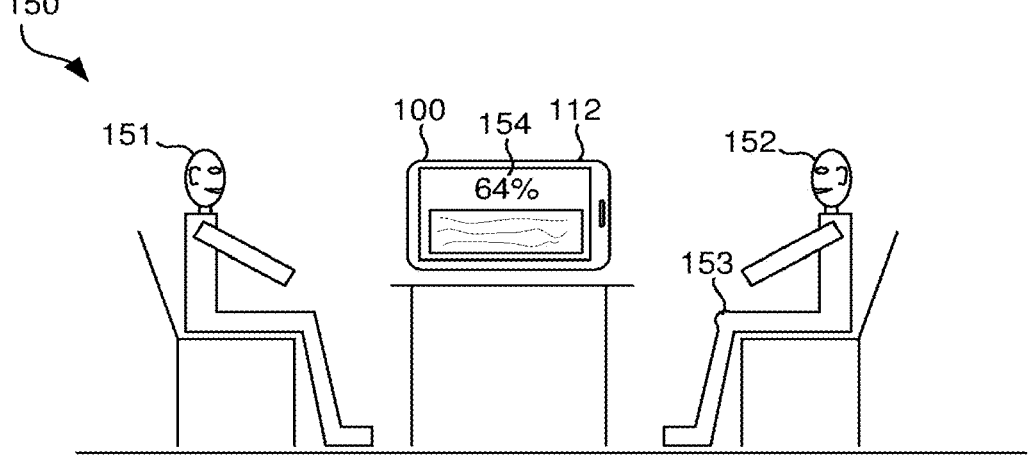
FIG. 1A illustrates a computer system 100 for managing patients of knee surgeries.
FIG. 1B illustrates a surgeon's consulting room where the computer system of FIG. 1A is in use.

FIG. 1B illustrates a surgeon's consulting room 150 where the computer system 100 of FIG. 1A is in use. Present in the room 150 are the surgeon 151 and the patient 152 with a swollen knee 153 that needs surgery. At the moment schematically captured in FIG. 1B patient 152 has provided patient input data to the computer device 100, that is a tablet computer in this example, and the processor 102 of the device 100 has calculated a predicted satisfaction value. Processor 102 has also generated an electronic document comprising a report and displays the electronic document on screen 112 of tablet 100. In particular, processor 102 generates, as part of the report, a graphical indication 154, such as a number or chart, of the predicted satisfaction value. Surgeon 151 can now discuss the value 154 with patient 152, which allows surgeon 151 to make changes to the operation procedure, care plan or manage the patient's 152 expectations to increase the chances of a positive outcome.

FIG. 2 illustrates a method 200 as performed by processor 102 for managing patients of knee surgeries. FIG. 2 is to be understood as a blueprint for the software program and may be implemented step-by-step, such that each step in FIG. 2 is represented by a function in a programming language, such as C++ or Java. The resulting source code is then compiled and stored as computer executable instructions on program memory 104.

Method 200 commences by generating 201 a pre-operative patient questionnaire user interface associated with a future knee operation of the patient.

FIG. 3 illustrates an example pre-operative patent questionnaire user interface 300 displayed on touch screen 112. The questionnaire interface 300 may be web-based, which means processor 102 is part of a web-server and generates the questionnaire interface 300 by writing HTML code to a data store that is accessible by a browser running on a patient device, such as a tablet computer. In another example, the questionnaire interface 300 is app-based, which means an app is installed on computer system 100 and processor 102 generates the questionnaire interface 300 by executing library functions that contain generic user interface functions.

FIG. 3 shows one page of the questionnaire 300 and the current page contains exactly one question 301 with multiple possible answers 302. Processor 102 monitors user interaction with respect to the user interface 300 and upon detecting user interaction with one of the multiple possible answers 302, processor 102 registers this answer and creates the next page of the questionnaire that again contains only a single question.

Processor 102 may register the selected answer by storing an answer value on data store 106, such as '1' if the patient selected 'Never', '2' if the patient selected 'Rarely' and so on. In the web-based example processor 102 sends the answer value to a server via XMLHttpRequest, POST or GET methods.

As a next step, processor 102 receives 202 patient input data indicative of answers of a patient in relation to the pre-operative patient questionnaire. This may mean the processor 102 receives the answer values from data store 106 or from a web-based interface via XMLHttpRequest, POST or GET methods. The patient input data may be identical to the answer values or may be pre-processed, such as by compression or encryption to obtain the patent input data.

In some examples, the patient input data is generated by a patient sensor and uploaded to the computer system 100. For example, the patient can wear a step counting device, such as a smart phone with a step counting app installed or a wrist or ankle sensor. Processor 102 then receives the step count from the step sensor and uses the step count just as the questionnaire data as if the patient had been asked about their activity level and answered in the number of steps.

Processor 102 then feeds the received patient input data into a statistical model to evaluate 203 the statistical model. This way, processor 102 determines a predicted satisfaction value indicative of satisfaction of the patient with the future knee operation.

FIG. 4 illustrates a statistical model 400 as stored on data memory 106. The statistical model 400 comprises nodes represented by discs and edges represented by arrows. The nodes are stored on data memory 106 and represent the patient input data, such as age node 401 and BMI node 402 and the predicted satisfaction value at output node 403. The nodes are stored an data memory 106 as a data structure, such as a list where new nodes are appended for example node list.append(new Node("Age")) for creating the age node 401. In this example, the label "Age" is unique such that the age node 401 can be retrieved by searching for this label node list.find("Age"), which returns a pointer to a Node object.

Similarly, the edges are also stored on data memory 106. The edges between the nodes represent conditional dependencies between the patient input data and the predicted satisfaction value. Edges are appended to a global edge list by edge list.append(new Edge(node list.find("Age"), node list.find("Satisfaction"))) to create a direct edge between the age node 401 and the satisfaction node 403.

In one example, the statistical model 400 is a Bayesian network, that is, a directed acyclic graph (DAG). In this example, the nodes represent random variables in the Bayesian sense: they may be observable quantities, latent variables, unknown parameters or hypotheses. Edges represent conditional dependencies; nodes that are not connected represent variables that are conditionally independent of each other.

Each node is associated with a probability function that takes, as input, a particular set of values for the node's parent variables, and gives (as output) the probability (or probability distribution, if applicable) of the variable represented by the node. For example, if m parent nodes represent m Boolean variables then the probability function could be represented by a table of $2^m$ entries, one entry for each of the $2^m$ possible combinations of its parents being true or false.

For example, there may be multiple age related nodes where each node is indicative of whether or not the patient age is within a predefined age bracket. Such as a true or false value for the statement "age is below 40". Other representations could include multiple sub-tables for groups of parent nodes with dependence upon each other.

In other examples, statistical model 400 is an undirected, and possibly cyclic, graph; such as a Markov network.

The satisfaction node 403 may also be a Boolean node representing whether or not the patient is satisfied with the operation. This way, the probabilities given the actual patient input data as described above can be propagated through the statistical model 400 to calculate a final probability for the patient being satisfied, that is, a probability for a value of '1' or 'True' at the final satisfaction node 403. This probability can then serve as the predicted satisfaction value. An example of this is that a BMI over 40 and age under 55 years would return a predicted satisfaction value of '64%', indicating that there is a 64% chance of the patient being satisfied after the operation, and that the relatively young age and high BMI has negatively impacted her chance for a successful outcome.

The example of FIG. 4 is a hierarchical model, which means that there is at least one path from the patient input data to the predicted satisfaction value 403 having at least two edges. For example, the path from age node 401 to satisfaction node 403 contains four nodes in total and three edges between them.

Finally, processor 102 generates 204 an electronic document comprising a surgeon report associated with the future knee operation to indicate to the surgeon the predicted satisfaction value.

In one example, processor 102 determines a statistical transformation of the predicted satisfaction value before generating the report, such as scaling the predicted satisfaction value to patient distributions of answers, such as the distribution of answers of other patients of the same doctor.

In further examples, the distribution of answers is drawn from one or more of:

postoperative outcome,
preoperative baseline,
healthy patient baseline,
postoperative high achievers, and
postoperative low achievers.

Processor 102 may further perform the statistical transformation by performing a conversion to odds ratio or risk factors.

Processor 102 may generate the surgeon report by generating a graphical depiction of one or more of:

boxes,
vertical bars,
horizontal bars,
graphical elements with a colour scale mapped visual output,
conversion to percentages,
embedding into customizable lines of text, and
specific highlighted risk factors indicated to patients.

FIG. 5 illustrates an example surgeon report 500. In this example, the statistical model 400 has multiple outputs. That is, processor 102 determines multiple predicted satisfaction values, which may be considered influencing factors of a final satisfaction value. In this example, processor 102 determines partial satisfaction values/influencing factors from the Knee injury and Osteoarthritis Outcome Score (KOOS) In particular, processor 102 determines a predicted pain value 501, a predicted symptoms value 502, a predicted function in daily living (ADL) value 503 and a predicted knee related quality of life (QOL) value 504.

Surgeon report 500 may further comprise a first indication 505 of patient input data, that is, answers selected by the patient, or summaries of those answers that affect the risk positively. This means these answers lead to a higher probability of patient satisfaction. For example, the patient answers that he has low severity and infrequent back pain. This makes him more likely to be satisfied with the knee operation than other patients with high severity and frequent back pains.

Similarly, report 500 comprises a second indication 506 of negative risk adjustments, such as poor mental health score, isolated lifestyle, smoker or high pain medication use.

Processor 102 determines the positive risk adjustments 505 and the negative risk adjustments 506 by selecting the patient input data that has a contributing value that is less than the final value. In other words, processor 102 compares the probability of the path from one patient input node to the output node to the final predicted value. If the edge probability is less than the final value, processor 102 selects that patient input node as a negative risk adjustment and vice versa for edge probabilities that are higher that the predicted value. Processor 102 determines the positive risk adjustments 505 and the negative risk adjustments 506 by selecting the patient input data that has been previously identified as having a positive or negative relationship with the perceived satisfaction value, in the context of other conditionally dependant inputs. These relationships could be predetermined and stored in a data table in data store 106 along with the appropriate text string to display.

Report 500 further comprises an indication of an activity level of the patient. In the example of FIG. 5 this indication is a chart with the number of steps displayed for each day before the surgery or consultation as a line 508. The chart 507 further comprises an indication of the variation 509 of the number of steps, which in this example comprises two horizontal lines to indicate a performance band for the patient, colour coded to indicate the activity level the patient is achieving relative to gender & BMI adjusted norms.

Report 500 further comprises an indication of the percentile 510 of the activity level of this patient within patients in this age group and gender and an average value 511.

FIG. 6 illustrates another example of the statistical model 600. This example is a data fed, supervised learnt model in order for processor 102 to calculate a prediction of a central node (in this case, postoperative self-reported pain). The nodes are binary, which means questions that are answered in the positive or other patient data that meets a predetermined criteria is illustrated as bold and connected. Each set of linked nodes defines a conditional probability table.

For example, in the fall group 602, the patient has answered that he had a fall in the last 12 months and therefore, the corresponding fall node 603 is illustrated in bold. The fall node 603 is connected to pain node 604 by edge 605 indicating that the fall in the last 12 months makes satisfaction with the level of post-operative pain less likely.

FIG. 7 illustrates the statistical model 600 from FIG. 6 in more detail. This may be the back end structure for pulling the prediction once learnt. Each circle in FIG. 7, such as circle 702 represents an independent Markov blanket JA of factors that processor 102 can fully define in a lookup table with little lag. The Markov blanket of a node contains all the variables that shield the node from the rest of the network. This means that the Markov blanket of a node is the only knowledge needed to predict the behaviour of that node.

An example of a calculation incorporating the lookup table structure defined in FIG. 7 would include the following: a prior probability for likelihood of satisfaction (80%), the patients age (64), gender ("Female"), current KOOS pain, symptoms & ADL score (38, 51 & 62) in the affected knee, specific answers to KOOS pain subsection question 2, 5 & 8 ("Mild", "Moderate" & "Severe"), falls in the last year (2), reported severity & frequency of back pain ("Severe" & "Daily") and presence of pain in the hip of the affected knee ("Yes"). For the calculation, processor 102 retrieves the lookup table of expected value based off the age and gender, KOOS pain results, other KOOS results & back pain, hip pain and number of fall results. These values are 84%, 72%, 77% & 47%. The equation may be as follows where n is the number of lookup tables used:

$$\frac{\sum\limits_{n}^{i=1} ExpectedValue_n (1 - prior)^{n-1}}{\sum\limits_{n}^{i=1} ExpectedValue_n \ (1 - prior)^{n-1} + \sum\limits_{n}^{i=1} (1 - ExpectedValue_n)prior^{n-1}}$$

Here this resolves to:

$$\frac{(84 \cdot 72 \cdot 77 \cdot 47) \cdot (20)^3}{(84 \cdot 72 \cdot 77 \cdot 47) \cdot (20)^3 \cdot (16 \cdot 28 \cdot 23 \cdot 53) \times (80)^3}$$

or a predicted satisfaction chance of 38.51%.

In a Bayesian network, the values of the parents and children of a node evidently give information about that node; however, its children's parents are also included, because they can be used to explain away the node in question. In a Markov random field, the Markov blanket for a node is simply its adjacent nodes.

Processor 102 can then calculate the joint probability from each table result by Pr(A|∂A, B)=Pr(A|∂A) where the blanket ∂A is the set of nodes composed of A's parents, its children and its children's other parents. This approach facilitates the processing of practically sized data sets.

The application front ends (patient & surgeon) as well as the web service may be implemented in C++. The database to store the nodes and edges and other data may be MySQL. A single database both holds the tables of predictive values to look up and patient records of the patient and their answer set. Processor 102 may execute a software called BayesiaLab by Bayesia S.A.S. for the predictive modelling.

FIG. 8 illustrates another example of a report 800. Report 800 interprets predicted satisfaction value as pain in order to reference the preoperative state against the postoperative. Report 800 comprises a pre-operative pain value 802. This value has been determined from placing the patients preoperative self reported pain level against the distribution of patients who've come into the surgeon's rooms. This is expressed as a percentile rank. In addition, report 800 comprises a post-operative predicted pain value 803. Processor 102 determines the post-operative value 803 by receiving patient input data before the operation as described above. This data is then used to place the patient against the same distribution in order to draw a predicted postoperative percentile rank Report 800 showed that the predicted percentile increases from 41% to 64% as a result of the operation. Report 800 also contains a brief explanation of the meaning of the other elements of the report.

FIG. 9 illustrates report 900, the result of an interactive element in report 800. Here the postoperative indicator arrow has the functionality of a button, changing the bar to a postoperative mode which has triggered an animated colour change in the percentile bar. Also triggered is the generation of an indication of positive risk adjustments and negative risk adjustments similar to the report in FIG. 5.

Referring back to FIG. 5, it is noted that in one example, the individual elements of the report may be customised or selected to be shown or not shown. In other words, the prediction front end is created in a modular manner to allow surgeon customization of what is shown and how it is shown.

FIG. 10 illustrates an example of a 'settings' back page 1000 allowing some customization of model weightings. The model weightings are broken into 3 groups ¬collective expert knowledge model 1002, individual surgeons' expert model 1003 and the data base model 1004. A user can adjust the weights by moving the respective slider and can adjust the 'yes' and 'no' weights for each of the questions from the questionnaire separately.

In other words, processor 102 generates the expert user interface 1000 comprising the expert data input 1002 to 1004 for expert input data indicative of the conditional dependencies between the patient input data and the predicted satisfaction value. Processor 102 receives the expert input data and determines the conditional dependencies between the patient input data and the predicted satisfaction value based on the expert input data. Finally, processor 102 stores the conditional dependencies as part of the statistical model on a data store 106 such that the conditional dependencies are based on expert network modelling and expert opinion as reflected by the expert input data. It is noted that the expert may be a surgeon, a patient, a nurse, a physiotherapist, a psychologist, or an allied health professional.

FIG. 11 illustrates a postoperative monitoring user interface 1100 for reporting step count of a patient 1102 against normalized expected recovery curves for very low 1103, low 1104, normal 1105 and high 1106 step counts. Additional data could be integrated into this postoperative monitoring interface such as sleep quality, heart rate & blood pressure. These could be displayed either textually as illustrated in FIG. 11 or via a custom display.

In one example, processor 102 further receives intra-operative data and post-operative data, such as through an additional user interface. For example, the deviation from the cut angle or any other inter-operative adjustments can be entered into the system 100 and after the knee operation processor 102 can then determine a revised predicted satisfaction value based on the intra-operative data and the post-operative data. The post-operative data may also be post-operative patient input data provided in a questionnaire.

Processor 102 may further determine a cost of an error as measured in terms of patient outcomes and may determine future outcome gains or losses. Processor 102 can then determine subsequent treatment decisions based on the future outcome gains or losses.

In some examples, the surgeon report comprises an indication of one or more of generic/holistic measures of health, specific functional attainments, postoperative range of motion, postoperative time to mobilisation, ambulation, activity level, and risk of adverse events.

Processor 102 may further perform a kinematic simulation of the knee joint, such as based on a mechanical model of the knee characterised by computer tomographic imagery. The simulation simulates the result of reconstruction of the total knee replacement. Processor 102 receives the kinematic simulation data from the simulator, such as by retrieving the simulation data from data store 106. The patient input data is indicative of activity desires or patient behaviour, and the nodes of statistical model comprise nodes representing the kinematic simulation data and the patient input data indicative of activity desires or patient behaviour.

For example, processor 102 may simulate the varus/valgus value of the knee, which can then become one of the nodes of the statistical model. The statistical model may further comprise nodes for activities, such as playing golf. A particular varus/values value may make playing golf more painful and therefore lead to a lower predicted satisfaction value, for example.

The methods described herein may also be used for operating a healthcare system. In particular, processor 102 may perform the method 200 in FIG. 2 to determine a predicted satisfaction value for each of multiple patients enrolled in the healthcare system. Processor 102 may then determine a patient care item for each of the multiple patients by maximising utility of healthcare spent in the healthcare system. For example, processor 102 may determine whether the cost for additional physiotherapy treatment outweighs the expected gain in predicted satisfaction value.

By combining the multiple patients at the same time, processor 102 can minimise the global overall cost with a collective satisfaction or patient outcome target and perform a per patient cost minimisation with a per patient satisfaction or patient outcome target. Processor 102 may also perform fixed global cost allocation with a satisfaction or patient outcome target maximisation.

Maximising utility may be based on a predetermined amount of cost expenditure for each of the multiple patients. For example, processor 102 may receive an indication that $10,000 can be spent on each patient and determines the optimal allocation of that amount in order to achieve the maximum predicted satisfaction value.

At the core of the issue of bias is a definitional difference between the surgeon and the patient's definition of what constitutes a successful surgery, and the failure to fully align patient expectations with the reality of their likely surgical outcome. One mechanism of eliciting a patient's measured outcomes is through the use of Patient Reported Outcomes Measures (PROMS).

A range of scoring metrics may be used which aim to strike different balances between incorporating objective, directly measurable data such as range of motion (ROM) measurements and subjective, questionnaire based data in order to elucidate and characterize patient dissatisfaction in a way that makes intervention feasible.

The advantages of the former are its reproducibility; however, the clinical relevance suffers in comparison to direct patient reported results. Another approach involves high levels of complexity in patient outcome questionnaires such that each question focuses on a very specific scenario or source of pain or dissatisfaction; however, this comes at the cost of exposure to survey fatigue or a reduction in the clinical practicality of administering the questionnaire. Further developments include attempts to resolve the clinical burden through an adaptive questionnaire format in order to get specific information that characterizes a patient's expectations and aspirations. While this approach is highly relevant to the aim of providing personalised medical care, it does lead to potential issues around database completeness for data analysis and patient outcome prediction work.

Examples of patient focused scores are the Knee Osteoarthritis & Injury Outcome Score (KOOS), the Oxford Knee Score (OKS) and the Western Ontario and McMaster Osteoarthritis index (WOMAC).

More general questionnaires include the SF-36, used in conjunction with a specific knee functional questionnaire. The final structure of scoring for TKA outcome looks directly at the satisfaction level of the patient, either by directly asking if they're satisfied with the surgical outcome, using a visual analog scale construct or generating a Patient Acceptable Symptom State (PASS) for an existing scoring structure to binarise the patient groups into either satisfied or unsatisfied groups.

Alignment of implant components to the bone may be a benchmark for measuring short term outcomes in Total Knee Arthroplasty, and this may correlate with survivorship. This reduces the knee replacement operation to one in which a simple mechanical optimization is all that is required to achieve a 'success', which may not equate to a satisfied patient. A variety of other factors, some surgical and some patient linked, may drive outcome.

Risk factor analysis for Total Knee Arthroplasty is one example, which may target one of two primary goals—either a risk factor identification approach (where the focus is on identifying singular key factors that are indicative of a major complication being probable) or outcome prediction (where the consideration is wider with regards to interdependency of input variables, at the cost of presenting a singular focus or isolating an intervention's impacts as accurately as possible). The endpoints targeted may be incidence of reoperation, length of stay greater than four days, readmission within one month and postoperative complications (orthopaedic and non-orthopaedic). A major advantage may arise if the data covers a single joint centre with a fairly large database of patient results. This controls for a number of variables that mixed-source datasets suffer from as confounding variables. On the other hand, the scope of the endpoints may be somewhat limiting, relying entirely on hospital based-admissions data and not (typically noisier, but more long term clinically relevant) PROMS measures. The statistical procedure of analysis, stepwise multivariate regression (with some filtering of inputs based off logistic univariate regression statistical significance) is one approach to risk analysis.

The data may comprise some noise by considering length of stay as a factor, and the endpoints are generally constructed around managing the cost of care in the short-medium term, likely capturing risk factors relating to infection or patients predisposed to present as dissatisfied regardless of the actual surgical outcomes. Psychiatric comorbidities present as the greatest single source predictor of negative outcomes for all endpoints considered. This, although not based off PROMS analysis, is useful in that it underscores even when considering for endpoints best designed to capture the impact of variables directly related to operative issues in surgery, the dominant factor in patient outcome is the presence of a psychiatric comorbidity—a factor related dominantly to the patient, rather than the surgery. This reasoning does not consider the likely causal contribution of a worse case of knee osteoarthritis acting as a contributing factor to a patient's psychiatric comorbidity risk, however, and it is worth noting that the input variables do not contain any radiographic or other preoperative osteoarthritic state variables.

Predicting patient reported outcome measures may be devised around the WOMAC score as both a preoperative input and a target prediction. The Short Form 36 Questionnaire (SF-36) may be used, as a validated, more general patient response centered health measure as an additional preoperative input to the standard demographic factors and socioeconomic factors. This approach may suffer somewhat from the issue outlined above if it considers patients recruited from joint centers in Australia, the United Kingdom and the United States. Each of these markets have fundamentally different healthcare regimes that affect a patient's surgical experience and characterise the demographics for the relevant patient groups selected (that is, it is not just the patient's experience in receiving a joint replacement but who was able to receive a joint replacement in each country.)

Although it may be possible to control for this as a factor, several distortions exist such as the US centers treating a much higher percentage of high income and high education patients. While the aims are to identify factors that survive these differences in order to characterise robust preoperative predictors, the presence of a limited but disparate sample of patients does not guarantee identified factors will be relevant to the population as a whole.

Some control may be achieved, however, by pursuing a hierarchical model rather than a regression based analysis, limiting the vulnerability of a regression model that may map itself to a non-linear population function that is only presenting some part of its structure with the selective sampling. In one example, the greatest single determinant of postoperative outcome in WOMAC's function and pain scores is the preoperative result for those same scores. This presents a question in terms of what it is capturing—do patients suffering from osteoarthritis to a greater degree prior to their operation have a worse outcome after surgery, or is it simply that patients who innately perceive their state to be worse continue to do so after surgery? The question begins to border on philosophy when considering the intent of the relevant PROMS scores (is it to present an objective as possible measure of a result that is only considered subjectively or is it to embrace the subjectivity of the patient's experience of their condition?) but does have relevance in the context of whether the better figure to consider from a machine learning perspective is the amount of patient improvement or their final state. Further, the SF-36's mental health subscore may be another key predictor presenting some support to the idea that patient perception is a factor, likely one which has seen some of its weight in this model absorbed in the preoperative WOMAC variables due to the inherent greater correlation the preoperative and postoperative scores are likely to have to each other than the results of another measurement instrument, even if the preoperative score is reflecting a correlative bias with the mental health score (the postoperative score being a strong correlation).

On a whole, this example underscores the tangled webs of causality that emerge when applying frequentist statistics methodology to a machine learning problem as complex as this. The impact of psychological distress may characterise some of the mental health score as a reversible issue following surgical intervention, though to what extent the causal link is the preoperative patient's knee state driving their low mental health score may be captured by radiographic or other osteoarthritis score based variables.

The interplay of measured factors as indicators of patient satisfaction and their interplay with geography and hence the relative sampling of those patients may be relevant. The EQ5D depression score may be considered in addition to the IMD-Index of Multiple Deprivation, an Oxford University score of the socioeconomic deprivation of an area measured across indices of income, employment, health deprivation and disability, education, skills and training, barriers to housing and services, crime and living environment.

The IMD may be a significant predictor. It does not seem that where a patient lives alone is sufficient to drive their TKR outcome as there is no credible causative link. The causative links that can be identified are a) a poorer quality of healthcare provided to those with a lower means, though the publicly managed nature of the healthcare systems suggests this isn't the key driver (notwithstanding some potential self selection of higher experience surgeons to more 'prestigious' hospital environments which could receive a patient group from an, on average, less deprived geographic locale), and b) a somewhat reduced 'drive' or other mental characteristic relating to patient rehabilitation conformance and outcome perception. The need to identify the driving factors in a set of predictors is less pronounced when considering a single predictive model in isolation, but if attempting to combine insights from models with separate controls and co-predictors it becomes an important tool in identifying what predictors being introduced are presenting unique, uncross correlated information in the absence of a full dataset to test this.

Mental traits that render a patient more or less susceptible to a poor postoperative outcome may also be characterised. A regression analysis relationship may be found between the WOMAC pain and functional score outcomes and the psychological attribute self efficacy, a measure of "the conviction that one can successfully execute the behavior required to produce the outcomes", in this case, of a successful TKR operation recovery. This can then be thought of as a derived attribute, in that it captures both the patient's assessment of their own willpower as balanced against their perception of the relative difficulty of the road to recovery. It may also capture some hidden correlations not captured in the variables, as the measure is likely to correlate with the delay the patient has allowed themselves to undergo before seeking treatment, and hence the severity of osteoarthritis at surgery.

Self-efficacy may be an independent predictor of patient outcome. As such, other mental attributes may be incorporated into the regression analysis, many of which have very high correlations and hence lead to some results vulnerable to misinterpretation. One such result is the high level of power given to anxiety to predict poor pain outcomes in the multivariate analysis, which is likely reflecting a combination of its correlation with depression and depressions own negative correlation with pain severity and the ceiling effect of the score. As such, it is important in regression based models to interpret the true independence of a predictor through the lens of what other factors it has been regressed with, while also understanding the many layers of abstraction that separate what is actually being assessed. At its core, in preoperative prediction it is the patient's psyche and its impacts on their response to their changing pain state that is under review, and the underlying factors that contribute to their response to surgery are no doubt imperfectly captured by static instruments tuned to measure rigidly defined psychological attributes.

Nevertheless, self efficacy is a useful factor to incorporate in that it captures psychological information explicitly linked to the patients osteoarthritic state and upcoming surgery (it is a measure of how capable they feel of overcoming specific challenges), something which more generic mental health scores do not touch upon. As such, studies are still able to identify self efficacy as a significant predictor of functional outcome, though not pain.

The causal link might be that greater pain is not in anyway mitigated by self efficacy, but the pain aversion based component of a patient's functional outcomes are—more self efficacious patients are better equipped to overcome pain in restoring their lifestyle. As an observation from this, it is worth keeping in mind the nature of PROMS scores in that their construction and categorization into subscores such as pain and function is not an attempt to isolate specific components of a patients experience post surgery, but to form a number of (sometimes subtly) different clinical perspectives with which to assess their outcomes. It is therefore interesting that the regression may not choose to use preoperative pain as a regressor for postoperative functional outcome or vice versa. It is reasonable to hypothesize that if self efficacy is capturing the capability of a patient to overcome pain-based disability postoperatively, then a patient with a much higher preoperative functional state than their pain state is one who is highly self efficacious and the addition of the additional score required to assess this pre-clinically is redundant. Relationships such as this, where existing clinical tools may partially capture elements of a relevant underlying factor isolatable in a separate instrument are precisely the application in which a machine learning rather than a linear regression based approach could advance the field of postoperative outcome prediction significantly.

Some further evidence exists that self efficacy is a major factor. A similar study assessing personality type with a validated instrument as a predictor of TKR showed personality types identified as 'unstable introverts' as being the least likely to express satisfaction post surgery. There may be a correlation of this personality typing with self efficacy and pain catastrophising behaviors, and the personality tests showing metrics of neuroticism and extraversion are presented as alternate categorical labels for tendency to catastrophise and self efficacy. Personality subtyping may be independent from self efficacy or other factors but instead some examples profile another instrument with a more discrete categorisation, acknowledging the problem of an enormous amount of psychological attributes, all of which are imperfectly captured by questionnaire instruments both in terms of design and in terms of response noise and even if they were captured perfectly with regards to their definitions, represent factors that are highly correlated.

As such, making decisions on which of these instruments are to be utilized requires considering multiple dimensions, with a limit to those to be included expressed in terms of the increasing noise in results as a result of survey fatigue and clinical practicality issues. The amount of correlation or predictive power contributed difficult to assess.

There may be an ability to separate several mental constructs such as optimism, pessimism, hope, treatment credibility and treatment expectancy into their constituent constructs be identified as independent factors and show that, despite enormous cross correlations, the individual psychological factors can be uniquely separated. However, incorporating a general factor into a five factor model may identify a better fit to the data, despite the presence of some specific variance, suggesting the clinical relevance of separating these unique mental constructs may be limited.

Another metric is called the Injustice Experiences Questionnaire (IEQ), adapted for TKR recipients. The questionnaire may cover three major aspects—do the patients consider their condition irreparable or believe that their life has been permanently negatively impacted, do they interpret it as being in some manner "unfair" and do they consider someone else partly at fault for their condition. One example is a stepped introduction of factors into a linear regression model, assuming they factor their wish to correlate has the least significance and is introduced last, aiming to predict WOMAC pain and function scores. Dominant factors may be presurgical pain and function scores, and it is worth keeping in mind that these scores may drown some of the significance of other psychological scores (as a patient's measure of their pain right now can be assumed to capture some level of the psychological factors dictating their likely pain response in the future.)

However, when analysed in univariate regressions, the IEQ may have a stronger correlation. It is worth considering the nature of the IEQ and the postoperative scores being considered here, however. The results for the IEQ questionnaire may be lower (by a factor of 2 to 3) to scores recorded in the questionnaires native domain of injuries and accidents. The patient group may be older and may be suffering from a degenerative condition without a salient source to direct their blame towards. As such, it is possible that the IEQ is acting as a filter for a relatively small amount of doomed-to-dissatisfaction patients, rather than a tool capable of categorizing patients across the breadth of outcomes.

This would lead to it identifying as a statistically powerful tool for regression as its numerical distribution of results (many low scores with a long tail of higher scores) is biased in a manner predisposed to fit with the ceiling effect and long tale of post-operative outcomes scores. It follows then that a relatively small number of very accurate predictions could be fueling a strongly reported fit. This is another application where a machine learning algorithm (even one as simple as a CART analysis) might produce more meaningful observations.

TKR satisfaction may be considered from the perspective of categorizing who is satisfied and who is not without a focus on prediction by allowing other postoperative variables to feed into the patient's prediction of satisfaction. The greatest 'predictor' of dissatisfaction may be when the patients expectations have not been met, more so than any other preoperative or postoperative factor.

The lens of a patient's presurgical expectations might be an effective way of 'gating' the many preoperative psychological attributes that may impact on outcomes into a single factor Patient expectations, as a major predictor, represent a very realistic pathway for future interventions towards improving patient outcomes by aligning patient expectations to their surgeons.

Overly optimistic patients who do not achieve their unrealistic expectations have a believable path to poor performance as a result of their mindset; similarly, overly pessimistic patients may be dooming themselves to a negative perception regardless of their actual surgical outcome. On another note, the ability to predict with some confidence a patient's outcome, and present it to them as slightly more optimistic than it actually is may push the patient towards better outcomes, ethical considerations notwithstanding.

Possible mechanisms to drive surgeon-patient expectation alignment begin with first measuring the expectation gap between surgeons and patients on a per patient level using a validated questionnaire instrument. This may comprise patient education classes or other information dispersion mechanisms to effect their impact on patient's preoperative expectations. Some examples use personalized reports or information in their educational structure. As such, they have necessarily incorporated an understanding of the patient decision making process into their design & development and an understanding of the psychosocial factors at work. By incorporating risk factors identified from a patient prior to their operation into a decision support tool for the patient with personalized risk factor evaluations, this gulf could potentially be bridged.

One example is looking at presurgical expectations and breaking it down into response expectancies and behavioral outcome expectancies. Response expectancies cover involuntary factors such as pain and ability to sleep. Behavioral outcome expectancies cover factors related to the patient's own decision making such as their capability to overcome specific barriers. The two factors are linked in a similar way to how self efficacy is linked to preoperative pain scores, but capture both factors in the context of the patients expectations preoperatively about the post-operative state. The results show that the behavioural outcome expectancies better predict pain severity and function at follow up than response expectancies do and outperforms other psychological attributes outside of pain catastrophising, lending further credence to the idea that incorporating some element of a patient's beliefs about their own capability tempers the noise found in purely psychological attribute based predictions.

Pain catastrophisation, as a potential predictor, may be further explored as well as a number of different preoperative indicators linked to psychological status including depression, generalized anxiety or panic disorder measures. This may mean the measure for pain catastrophisation could binarize the results of the pain catastrophisation score into a 'high' or 'low' bin and may result in segmenting the highest tertile of the patient population into the high pain catastrophisation population group. This example may also take the route of characterizing its results in a logistic regression with its improvement scenario based off a percentage gain on the initial state.

It is important to note the continued role surgical factors and surgical incidents, including infection rates, ROM achieved on the table while operating, to some degree achieved alignment (in so far as extreme mal-alignment may cause a negative impact) and surgeon training and volume of operations are all drivers of patient outcome not available at the time of making a preoperative outcome prediction, and so there may be a level of 'gap' that predictive models may not close. Prolonged operating time as a broad catch all predictor for surgery complications also has predictive power, though the causality that results is unknown and might be inappropriate if acted on directly.

There are five dimensions across which separate contexts are prevented from being synthesized into effective clinical tools.

The first of this is the target population, with significant variations observed across fundamentally different healthcare regimes that affect a patient's surgical experience and characterize the demographics for the relevant patient groups selected (that is, it is not just how the patient's experience in receiving a joint replacement but who was able to receive a joint replacement in each country.)

The second is the nature of the PROMS or satisfaction metric used and protocol biases in how it is applied (self-administered vs guided, for example.)

The third is whether satisfaction itself or PROMS are actually the target metric at all, as these correlations have been shown to be moderate to weak and the functional and pain states of the patient postoperatively contribute holistically to satisfaction.

The fourth is how a successful PROMS result is defined and whether it is an absolute outcome score that can be considered to succeed or a relative improvement from a preoperative state.

Finally, the use of different instruments in defining the predictor variables and confusion about the constructs they represent, particularly in the psychological area makes comparison of studies with disparate results even more troublesome.

One facet of the patient's disease state that functional instruments seek to capture is the degree of impairment and lost mobility brought on by OA. Patient activity levels may be undertaken using subjective self assessment using a number of different developed scales or, surgeon 'demand matching' of the patient.

Subjective self reported measures of activity and mobility level may vary greatly from objective measures in non predictable ways, however, with sub population trends and variable subject level bias both skewing results. End stage knee osteoarthritis patients may have reduced steps/day counts over healthy comparable age subjects, dropping from about 8800 steps at peak to 6600. These figures are variable within and between patient population groups, however, with delimitations such as public vs. privately treated patients, age and gender all creating enormous variance. Seemingly at odds with this variation is the observation that only 3 days of active measurement are required to elicit a patients activity level profile when assessing step count, which would seem to dispute the idea that patients will change behaviour on weekends vs weekdays and other distinguishing factors.

The objective measurement of activity level can be done in a number of ways. Step count is the most directly applicable to patient lifestyles, to the point where in rheumatoid arthritis sufferers it can be used as an assessment of treatment outcome. Other examples look at activity monitor data as defined by some other metric than step count, including the % of the day the subject spent moving or upright.

Such measures can be considered to be measuring different constructs to step count, however, as it is not difficult to imagine a scenario in which subjects who are active and walking for the same amount of time achieve different step counts based on gait speed. Other examples use accelerometry based at specific points, and correlate accelerometry data from the tibial tubercle to patient reported knee instability. Gait analysis may also be useful. Step count has a significant advantage in that the variable it introduces is readily understood and so empowers patient self management of their disease state.

Wearable wireless activity monitors such as the Fitbit are an increasingly low cost, clinically relevant off the shelf option for monitoring patient activity levels. These devices may be valid and reliable assessment tools for ambulation in normal subjects specifically, and the whole field of pedometry generally may have similar effectiveness. Other examples exploit the value of wireless activity monitors in chronic disease assessment The period over which the devices where worn may be 48 hours.

One example reports on energy expenditure quantification based on an intelligent activity monitoring device. This may comprise a measure of activity level over 5 different recording periods, covering preoperative, 6 week, 3 month, 6 month and 12 month scenarios. This may allow for a single value that is patient relevant, understandable and readily intervenable by patients in a self managed way to be reported, an argument that has been noted previously.

The device may measure the amount of time spent walking as a percentage of daily activity and there may be an implicit relationship between time spent walking, speed of gait and amount of steps being undertaken. As a demonstrative example, a patient who had spent 5% of the day walking pre and postoperatively, whose gait speed was twice as fast postoperatively, would count twice as many steps with a pedometer in the postoperative scenario but the same amount of time spent walking. Other examples assess patients over a 4 to 7 day period using a relatively small and unobstructive waist mounted device and so represent an attempt to overcome some of the potential observation bias. This may comprise sampling differences, including a BMI.

These measures could be used as an assessment target for early recovery interventions designed to drive patient self-efficacy, and so with such a structure a clinical improvement mechanism could be generated.

One example are BBN models. Particularly appealing in this structure is the relative ease with which expert knowledge modeled observations can be pulled into the model to enhance its predictive capacity and avoid some of the issues associated with the fractured nature of the available data in the literature. These observations can be pulled from either expert individuals, teams or through literature meta analysis.

As a further point, Bayesian models have an additional advantage in that the Bayesian Network structure can be quite insensitive to variation of precision of diagnosis.

Health care systems have a finite pool of resources in which to provide care to its citizens. Total knee arthroplasty is a surgery that is associated with high costs and a high rate of dissatisfaction at one year post operatively. Health care systems may benefit from a means in which the cost of a knee replacement is a) predictable for each patient and b) presents a pre and post-operative plan that is both cost effective and benefit maximising for patients. Stratification of patient care based on predictions of outcome pre and post operatively may offer a solution in which resources are effectively utilised pre and post total knee arthroplasty.

Stratification of care structures may benefit from a suite of targeted intervention strategies with known or predictable impacts on patient outcome. Using preoperative and postoperative data collection from patients maybe one mechanism by which cost effective, patient specific intervention strategies may be targeted at appropriate patients for maximal impact. Linking these observations to a healthcare utility filter may allow for significant savings to be realised, or significant outcome gains to be generated. Some possible approaches to achieving such a health care utility filter may be minimising the cost to the health system with a targeted overall patient satisfaction level, reducing associated individual patient costs with a targeted minimal acceptable predicted outcome per patient or a fixed cost, best allocation system whereby a fixed amount of resources are applied in order to get the highest possible proportion of satisfied patients.

As such, the solution proposed herein may overcome the fractured data landscape by pulling in observations from as many literature sources as possible to enhance an initial, single database fed model, using a team of surgeons to guide the development of the model in order to create as strong a predictor of TKR outcome as possible. Cheaply objectively measurable data sources may be used to substitute subjective data in the field of preoperative functional assessment relying on low cost pedometers in a clinically integrated workflow. The impact of the predictive tool may be assessed by way of expectation measurement of the patient prior to and following a routine surgical consultation in which this may be used to drive an intervention. Further to this, the impact across a patient group may be assessable through cost savings or outcome improvements across the participating patient population, by incorporating further elements described below.

In one example, there is a platform for collection of data from patients in a preoperative setting in order to predict postoperative outcomes in TKR patients against an analytical algorithm. The platform comprises an interface developed for maximal ease of patient use, using a one-question-per-page structure and automatic validation of incoming data where appropriate capable of rendering questions which are Visual Analog Scale Binary or multiple choice Open text or number fields Customizable on a per surgeon, per practice or per site basis An application to display the interface to the patient, capture patient data and return it securely to a server Customisation of the outcome to be predicted from patient reported outcomes in functional, activity, quality of life or pain based subdomains, generic/holistic measures of health or specific functional attainments including but not limited to postoperative range of motion, postoperative time to mobilisation and ambulation or activity level and risk of adverse events.

There is provided development of the algorithm so utilised in a Bayesian probabilistic structure or belief network comprising one or multiple of:

A database-fed model using known, logged outcomes to drive prediction

A user sourced expert knowledge model based off clinical observations and judgement of surgeons, nurses, patients and allied health professionals or groups thereof Development of a Bayesian decision tree or other decision tool to dictate or guide the implementation of preoperative intervention in order to drive improved outcome, or withdrawal of standard care practices in order to stratify patient care where deemed appropriate, comprising one or multiple of:

A database-fed model using known, logged outcome enhancements linked to interventions based off preoperative indicators to drive targeted intervention A user sourced expert knowledge model based off clinical observations and judgement of surgeons, nurses, patients and allied health professionals or groups thereof A customization structure for the underlying algorithm allowing a prediction that is probabilistically weighted between one or many such data or expert user fed models, able to be set to specific user selected weightings on a per surgeon or user basis A commercialisation platform for licensing or commercial ownership of the expert user algorithms so developed to other expert users.

There is further provided an interface for display of the predictions so generated to patients and expert users in a consultation or patient management environment comprising a set of customizable surgeon-user selectable modules capable of rendering Predictions for the various outcome targets, undergoing various statistical transforms including Scaling to patient distributions of answers drawn from a variety of distributions such as postoperative outcome, preoperative baseline, healthy patient baseline, postoperative high achievers or postoperative low achievers Conversion to odds ratio or risk factors Predictions undergoing various display structural changes such as Boxes, vertical or horizontal bars with a colour scale mapped visual output Conversion to percentages or embedding into customizable lines of text Specific highlighted risk factors indicated to patients An integrated measurement of patient expectations in order to assess the impact of the prediction tool on patient expectation management A remotely useable, web or app tool integrating the predictions and observations in order to provide a patient specific decision aid or report of likely outcome and current state, incorporating all of the customizability of display outlined above.

There is provided monitoring of post-operative patient data measurements that predict the pre-operative model.

There is provided post operative patient data collected at various time points post total knee replacement surgery that:

Informs the surgeon whether the patient is performing as expected

Informs the patient how they are performing compared to the patient population

Feedback to the pre-operative database to constantly improve accuracy of predictive software Post operative interventions based on post-operative data Post operative interventions may be triggered depending on post operative PROM's data that is collected:

Interventions triggered if the patient is under-performing increase contact with health professionals. Examples of this include review by a surgeon, physiotherapist, general practitioner and/or a psychologist Interventions triggered if the patient is performing well will encourage self management rehabilitation using a mobile technology interface Post operative stratification of care based on pre-operative and post-operative data collection with or without a cost-utility function driving the intervention selection.

Pre-operative data collection may stratify patients as to what their rehabilitation plan would likely be post operatively. Examples of rehabilitation could be self-management via mobile technology interface, rehabilitation with a Physiotherapist or cognitive behavioural therapy with a Psychologist. Where appropriate, these interventions may be commenced preoperatively rather than postoperatively.

There is provided a patient mobile application based compliance model facilitating self-management pre and post total knee replacement surgery.

Mobile application that provides expectation management, education, advice and exercise prescription for a patient who plans to undergo and has undergone total knee replacement surgery Exercise, advice and description will be patient specific depending on their input of exercises completed, step count and pain scores.

FIG. 12 illustrates an architecture 1200 for managing patients of knee surgeries. Input data of architecture 1200 comprises a simulator data 1201 from a simulator, such as a physical simulator that simulates movement of the bones around the knee joint.

Input data further comprises patient data 1202, such as data from existing data bases and data collected from patient interfaces described herein. Input data further comprises unknown data 1203 and expert opinion data 1204 from orthopaedic surgeons, physiotherapists and nurses, for example.

A knowledge generation module 1205 receives the input data 1201, 1202, 1203 and 1204 and generates a new body of knowledge of predicting patient outcomes post knee surgery. An amalgamation module 1206 amalgamates, based on a mathematical algorithm, the knowledge and data into a clinically useful and relevant tool. In particular, the amalgamation module 1206 determines the conditional dependencies between the input data, such as the patient input data, and the predicted satisfaction value as stored associated with the edges of the statistical model.

A patient interface module 1207, such as a patient interface environment and consultation application, generates a user interface comprising a patient questionnaire and evaluates the statistical model to determine a predicted patient satisfaction value as described herein with reference to FIG. 2, for example. That is, a patient specific program provides a patient with their likely predicted outcome based on a pre-operative survey.

The output data of the patient interface module 1207 is provided to a filter module 1208, such as a health care utility filter, which determines an action based on the predicted satisfaction value.

The filter module 1208 may activate a rehabilitation plan module 1209 that determines a patient specific post-operative rehabilitation plan. For example, the rehabilitation plan module 1209 may query a look-up table to find a pre-configured rehabilitation plan for a particular predicted satisfaction value.

The filter module 1208 may further activate a interventions module 1210 that determines patient specific pre-operative interventions. Again, processor may query a look-up table to find appropriate interventions.

The filter module 1208 may further activate patient guidance module 1211 that generates a patient user interface environment for self-management and education pre- and post-operatively. For example, the patient user interface may display instructions containing text, images and videos for knee-related and patient specific exercises and provide input fields that allow the patient to indicate the completion of those exercises.

Filter module 1208 may further activate a modification module 1212 that modifies expectations and enhances shared decision making, such as by informing the patient or the surgeon or allow the surgeon to collaborate with other surgeons to improve the expected outcome of the knee surgery.

Architecture 1200 further comprises a data collection module 1213 that continually collects patient data, such as pain scores, step count, KOOS. Data collection module 1213 may further collect data indicative of adverse events which will modify the patient interface environment 1211 and health care utility filter 1208.

Architecture 1200 is described as comprising several modules and each module may be a piece of software, such as a C++ or Java class or may be its own application executed by its own processor on its own device. The arrows in FIG. 12 may be implemented by way of function parameters, class parameters, inter-process communication, TCP/IP communication over the internet or another distributed computing platform, such as a cloud computing platform.

FIG. 13 illustrates a model selection user interface 1300 as generated by processor 102. The model selection user interface 1300 comprises multiple indications associated with respective models. For each model, the user interface

1300 shows the name of the surgeon, the name of the hospital, the number of patients used to train the model and the cost.

Each of the models is associated with different conditional dependencies between the nodes of the statistical model as learned from the data from the number of patients.

Processor 102 receives from a surgeon user input in relation to one or more of the multiple indications associated with one or more of the models, such as an indication of the surgeon pressing one of the 'select' buttons.

Processor 102 determines a price value associated with the one or more of the models, such as by retrieving the price value from a data base of models. Processor 102 then generates a payment interface for the determined price value, such as by calling a payment processor API, such as the PayPal API or Google Wallet API.

Once processor 102 receives a payment confirmation from the API, processor 102 enables the evaluation of the selected model, that is, processor 102 allows the patient data to be fed into the nodes and edges to determine the predicted satisfaction value.

It will be appreciated by persons skilled in the art that numerous variations and/or modifications may be made to the specific embodiments without departing from the scope as defined in the claims.

It should be understood that the techniques of the present disclosure might be implemented using a variety of technologies. For example, the methods described herein may be implemented by a series of computer executable instructions residing on a suitable computer readable medium. Suitable computer readable media may include volatile (e.g. RAM) and/or non-volatile (e.g. ROM, disk) memory, carrier waves and transmission media. Exemplary carrier waves may take the form of electrical, electromagnetic or optical signals conveying digital data steams along a local network or a publically accessible network such as the internet.

It should also be understood that, unless specifically stated otherwise as apparent from the following discussion, it is appreciated that throughout the description, discussions utilizing terms such as "estimating" or "processing" or "computing" or "calculating", "optimizing" or "determining" or "displaying" or "maximising" or the like, refer to the action and processes of a computer system, or similar electronic computing device, that processes and transforms data represented as physical (electronic) quantities within the computer system's registers and memories into other data similarly represented as physical quantities within the computer system memories or registers or other such information storage, transmission or display devices. It is noted that while the above examples relate to knee surgeries, methods and systems described herein may equally be applicable to other clinical procedures, such as hip replacements.

The present embodiments are, therefore, to be considered in all respects as illustrative and not restrictive.

The invention claimed is:

1. A method for managing patients of knee surgeries, the method comprising:

receiving patient input data indicative of activity desires or patient behaviour;

performing a kinematic simulation by a simulator that simulates a result of a future knee operation of a patient to determine kinematic simulation data;

evaluating by a processor of a computer system a statistical model to determine a predicted satisfaction value indicative of satisfaction of the patient with the future knee operation, the statistical model comprising:

nodes stored on data memory representing the patient input data and the predicted satisfaction value and representing the kinematic simulation data and the patient input data indicative of activity desires or patient behaviour, and edges stored on data memory between the nodes representing conditional dependencies between the patient input data and the predicted satisfaction value, wherein each stored node is associated with a probability function that is configured to receive as an input of values for parent variables as defined by the stored edges, and is further configured to produce as an output a probability of a variable represented by that stored node; and generating an indication of the predicted satisfaction value.

2. The method of claim 1, further comprising generating an indication of activity level for the patient.

3. The method of claim 1, further comprising:

determining, based on the patient input data, quantitative indications of influencing factors.

4. The method of claim 3, wherein the influencing factors include one or more factors from a Knee injury and Osteoarthritis Outcome Score (KOOS).

5. The method of claim 1, further comprising:

generating an electronic document comprising a surgeon report associated with the future knee operation to indicate the predicted satisfaction value.

6. The method of claim 5, wherein the statistical model is a Bayesian Network.

7. The method of claim 5, wherein the generating the surgeon report comprises determining a statistical transformation of the predicted satisfaction value.

8. The method of claim 5, further comprising:

automatically determining an intervention procedure based on the predicting satisfaction value, wherein generating the surgeon report comprises generating an indication of the intervention procedure.

9. The method of claim 1, further comprising:

generating, after a knee operation, a post-operative patient questionnaire user interface associated with the knee operation;

receiving post-operative patient input data indicative of answers of the patient in relation to the post-operative patient questionnaire; and determining updated conditional dependencies between the patient input data and the predicted satisfaction value based on the post-operative patient input data.

10. The method of claim 1, further comprising:

receiving intra-operative data and post-operative data; and determining, after a knee operation, a revised predicted satisfaction value based on the intra-operative data and the post-operative data.

11. A non-transitory computer readable medium with program code stored thereon that, when installed on a computer, causes the computer to perform the steps of:

receiving patient input data indicative of activity desires or patient behaviour;

performing a kinematic simulation by a simulator that simulates a result of a future knee operation of a patient to determine kinematic simulation data;

evaluating by a processor of a computer system a statistical model to determine a predicted satisfaction value indicative of satisfaction of the patient with the future knee operation, the statistical model comprising:

nodes stored on data memory representing the patient input data and the predicted satisfaction value and representing the kinematic simulation data and the patient input data indicative of activity desires or patient behaviour, and edges stored on data memory between the nodes representing conditional dependencies between the patient input data and the predicted satisfaction value, wherein each stored node is associated with a probability function that is configured to receive as an input of values for parent variables as defined by the stored edges, and is further configured to produce as an output a probability of a variable represented by that stored node; and generating an indication of the predicted satisfaction value.

12. The non-transitory computer readable medium of claim 11, the steps further comprising generating an indication of activity level for the patient.

13. The non-transitory computer readable medium of claim 11, the steps further comprising:

determining, based on the patient input data, quantitative indications of influencing factors.

14. The non-transitory computer readable medium of claim 13, wherein the influencing factors include one or more factors from a Knee injury and Osteoarthritis Outcome Score (KOOS).

15. The non-transitory computer readable medium of claim 11, the steps further comprising:

generating an electronic document comprising a surgeon report associated with the future knee operation to indicate the predicted satisfaction value.

16. The non-transitory computer readable medium of claim 14, wherein the statistical model is a Bayesian Network.

17. The non-transitory computer readable medium of claim 15, wherein the generating the surgeon report comprises determining a statistical transformation of the predicted satisfaction value.

18. The non-transitory computer readable medium of claim 15, the steps further comprising:

automatically determining an intervention procedure based on the predicted satisfaction value, wherein generating the surgeon report comprises generating an indication of the intervention procedure.

19. The non-transitory computer readable medium of claim 11, the steps further comprising:

generating, after a knee operation, a post-operative patient questionnaire user interface associated with the knee operation;

receiving post-operative patient input data indicative of answers of the patient in relation to the post-operative patient questionnaire; and determining updated conditional dependencies between the patient input data and the predicted satisfaction value based on the post-operative patient input data.

20. The non-transitory computer readable medium of claim 11, the steps further comprising:

receiving intra-operative data and post-operative data; and determining, after a knee operation, a revised predicted satisfaction value based on the intra-operative data and the post-operative data.

* * * * *